US012589026B2

(12) United States Patent
Egloff et al.

(10) Patent No.: US 12,589,026 B2
(45) Date of Patent: Mar. 31, 2026

(54) MICRO DOSING DEVICE AND METHOD OF ASSEMBLY OF THE MICRO DOSING DEVICE

(71) Applicant: SHL MEDICAL AG, Zug (CH)

(72) Inventors: Christoph Egloff, Neuhausen am Rheinfall (CH); Samuel Wyler, Abtwil (CH); Urs Jann, Nacka Strand (CH); Ralph Sommer, Neuhausen am Rheinfall (CH)

(73) Assignee: SHL Medical AG, Zug (CH)

( * ) Notice: Subject to any disclaimer, the term of this patent is extended or adjusted under 35 U.S.C. 154(b) by 583 days.

(21) Appl. No.: 18/015,377

(22) PCT Filed: Jul. 12, 2021

(86) PCT No.: PCT/EP2021/069380
§ 371 (c)(1),
(2) Date: Jan. 10, 2023

(87) PCT Pub. No.: WO2022/013172
PCT Pub. Date: Jan. 20, 2022

(65) Prior Publication Data
US 2023/0277375 A1     Sep. 7, 2023

Related U.S. Application Data

(60) Provisional application No. 63/052,963, filed on Jul. 17, 2020.

(30) Foreign Application Priority Data

Sep. 8, 2020    (EP) ..................................... 20195129

(51) Int. Cl.
*A61F 9/00*      (2006.01)
*A61M 5/168*     (2006.01)
(Continued)

(52) U.S. Cl.
CPC ....... *A61F 9/0017* (2013.01); *A61M 5/16809* (2013.01); *A61M 5/204* (2013.01); *A61M 5/31515* (2013.01); *A61M 5/3155* (2013.01)

(58) Field of Classification Search
CPC ............ A61M 5/16809; A61M 5/1424; A61M 5/31593; A61M 5/204; F04B 7/06
See application file for complete search history.

(56) References Cited

U.S. PATENT DOCUMENTS

| | | | | |
|---|---|---|---|---|
| 5,304,153 A | * | 4/1994 | Tsujikawa | ........... A61M 5/1424 |
| | | | | 604/288.02 |
| 5,906,597 A | * | 5/1999 | McPhee | .............. A61M 5/1424 |
| | | | | 251/5 |

(Continued)

FOREIGN PATENT DOCUMENTS

| | | |
|---|---|---|
| CN | 102648877 A | 8/2012 |
| CN | 104703640 B | 4/2018 |

(Continued)

OTHER PUBLICATIONS

International Search Report and Written Opinion for Int. App. No. PCT/EP2021/069380, mailed Aug. 27, 2021.

*Primary Examiner* — Laura A Bouchelle
(74) *Attorney, Agent, or Firm* — McDonnell Boehnen Hulbert & Berghoff LLP

(57) ABSTRACT

A micro dosing device is presented for delivering a metered dose of a therapeutic fluid having a dosing unit with a dosing chamber, a connector unit at a distal end for fluidly connecting a medicament container to the dosing chamber, a connector unit at a proximal end for fluidly connecting the dosing chamber to a medicament delivery member, and an activation mechanism, wherein the dosing chamber is configured to receive and therapeutic fluid. Further, the micro dosing device can have a dosing mechanism which provides an exactly metered dose of fluid to be expelled by the (Continued)

medicament delivery member, when the activation mechanism is triggered by a user.

19 Claims, 23 Drawing Sheets

(51) Int. Cl.
    *A61M 5/20*      (2006.01)
    *A61M 5/315*    (2006.01)

(56)            References Cited

U.S. PATENT DOCUMENTS

| | | |
|---|---|---|
| 6,213,981 B1 | 4/2001 | Hiejima et al. |
| 7,918,825 B2 | 4/2011 | O'Connor |
| 8,905,970 B2 | 12/2014 | Bates et al. |
| 8,998,850 B2 | 4/2015 | Kamen et al. |
| 9,399,102 B2 | 7/2016 | Dewoolfson et al. |
| 9,724,461 B2 | 8/2017 | Gray |
| 9,867,929 B2 | 1/2018 | Searle et al. |
| 10,159,807 B2 | 12/2018 | Cowe |
| 10,413,672 B2 | 9/2019 | Weibel et al. |
| 2003/0229310 A1 | 12/2003 | Flaherty et al. |
| 2010/0076370 A1* | 3/2010 | Howlett ............ A61M 5/31511 604/65 |
| 2012/0330235 A1 | 12/2012 | Moga et al. |
| 2014/0039396 A1 | 2/2014 | Geipel et al. |
| 2015/0140669 A1 | 5/2015 | Boehm et al. |
| 2015/0265775 A1 | 9/2015 | Cowe |
| 2017/0354778 A1 | 12/2017 | Gray |
| 2019/0224410 A1 | 7/2019 | Gray et al. |
| 2019/0275241 A1 | 9/2019 | Ring et al. |

FOREIGN PATENT DOCUMENTS

| | | |
|---|---|---|
| CN | 109045415 A | 12/2018 |
| CN | 110177597 A | 8/2019 |
| DE | 202011108638 U1 | 3/2013 |
| EP | 0523456 B1 | 12/1997 |
| EP | 2219707 B1 | 10/2018 |
| EP | 2903667 B1 | 7/2019 |
| EP | 2698178 B1 | 5/2020 |
| JP | 2017524677 A | 8/2017 |
| WO | 02/40083 A2 | 5/2002 |
| WO | 2011/163574 A1 | 12/2011 |
| WO | 2014/053848 A1 | 4/2014 |
| WO | 2016181384 A2 | 11/2016 |
| WO | 2018/132188 A1 | 7/2018 |
| WO | 2019121123 A1 | 6/2019 |
| WO | 2019/173785 A1 | 9/2019 |

* cited by examiner

243a

264c

264d

264b

264a

2631

264

243b

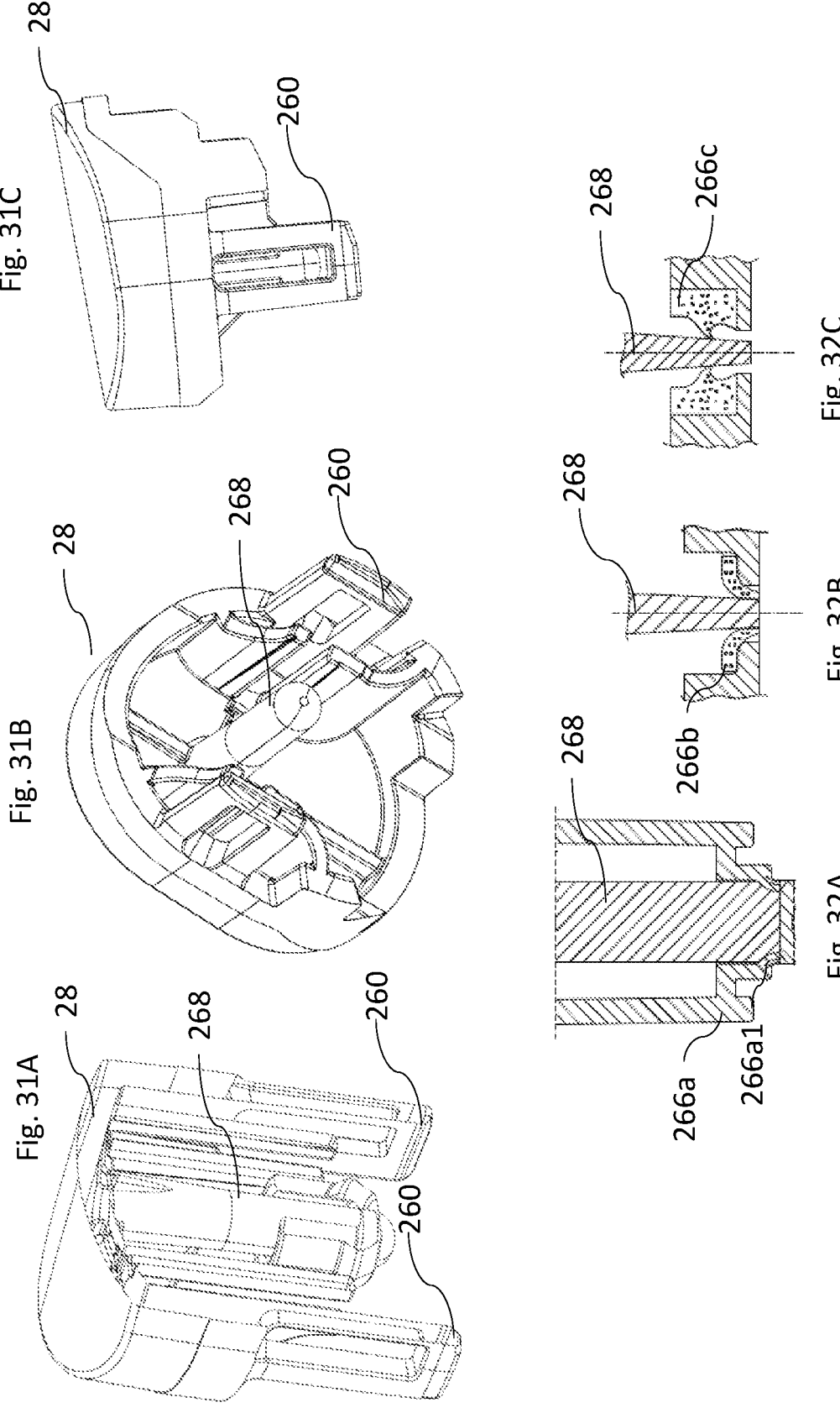

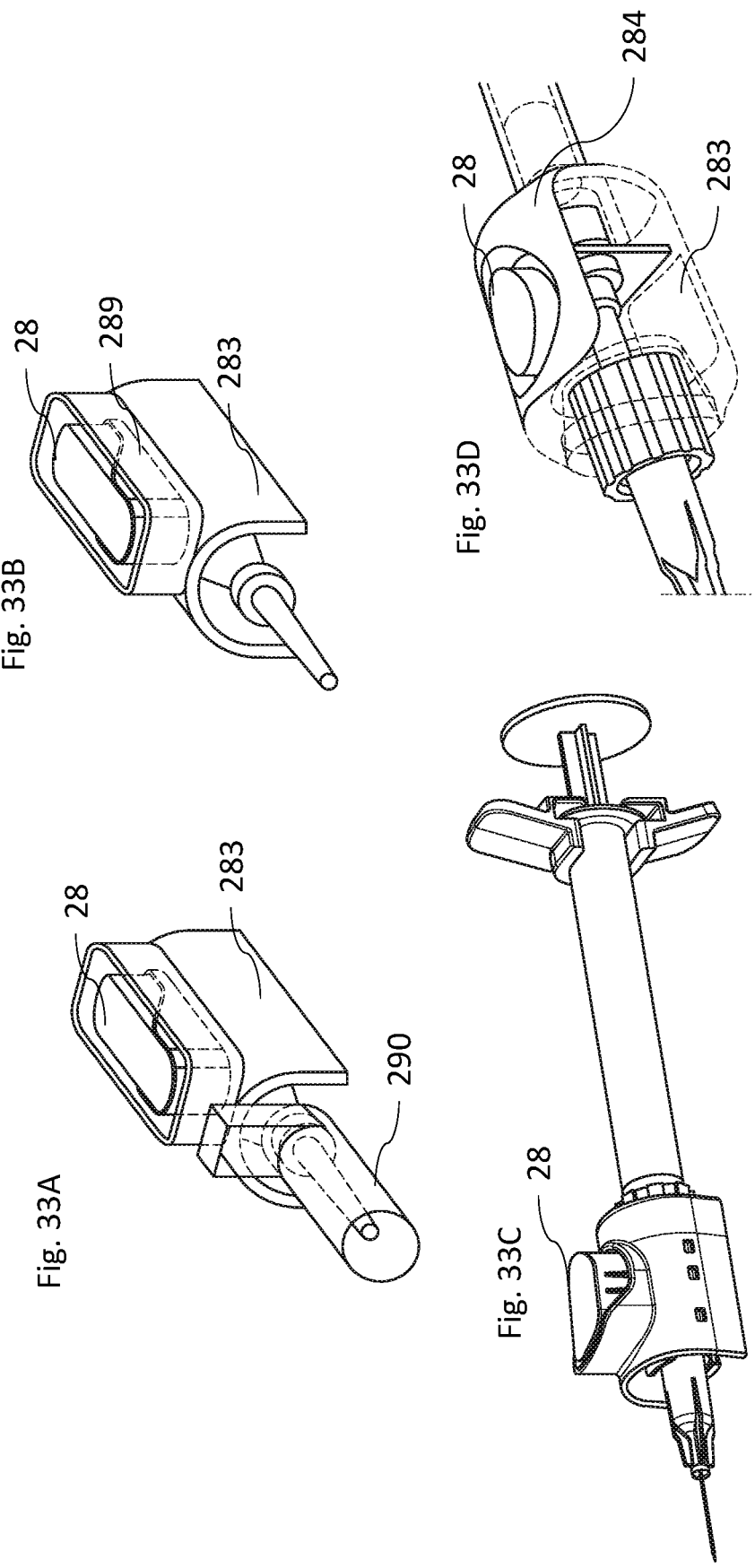

Fig. 34A
Fig. 34B
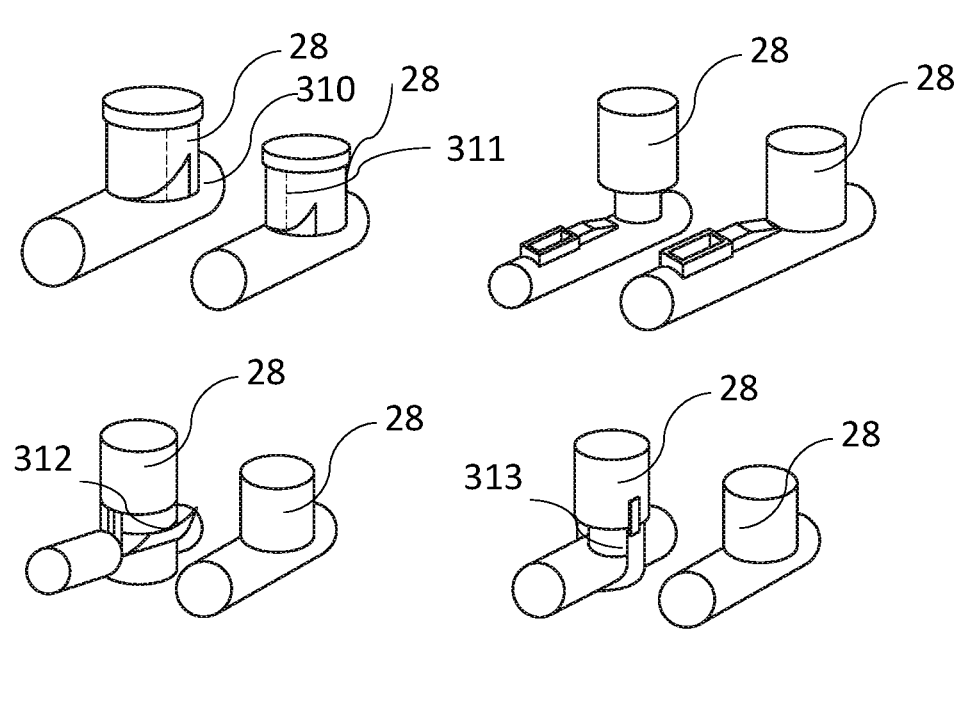
Fig. 34C
Fig. 34D
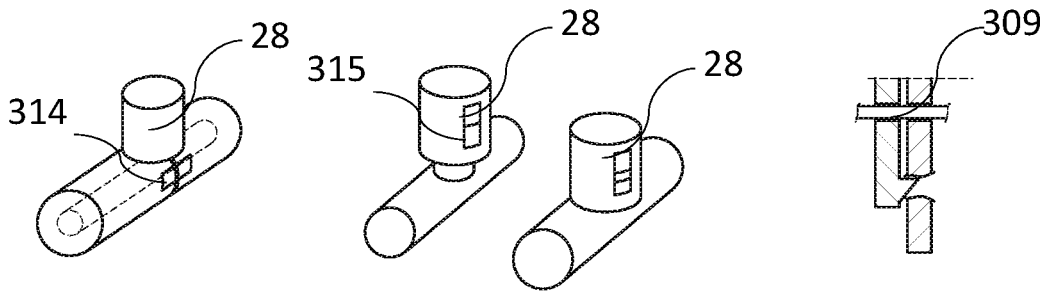
Fig. 34E          Fig. 34F          Fig. 34G

MICRO DOSING DEVICE AND METHOD OF ASSEMBLY OF THE MICRO DOSING DEVICE

CROSS REFERENCE TO RELATED APPLICATIONS

The present application is a U.S. National Phase Application pursuant to 35 U.S.C. § 371 of International Application No. PCT/EP2021/069380 filed Jul. 12, 2021, which claims priority to U.S. Patent Provisional Application No. 63/052,963, Jul. 17, 2020 and European Patent Application No. 20195129.0 filed Sep. 8, 2020. The entire disclosure contents of these applications are herewith incorporated by reference into the present application.

TECHNICAL FIELD

The present disclosure is directed to a device and method for delivering a therapeutic material for example an ophthalmic solution to an eye.

BACKGROUND

Known medicament dosing delivery devices, for example in document U.S. Pat. No. 5,304,153A, describe apparatus for the self-dosing of a liquid medicine. The apparatus includes a chamber formed in a casing for receiving a liquid medicine to be self-dosed by a patient, with an inlet and outlet port formed to communicate with the chamber free from leakage of the medicine. The apparatus further includes a piston fitted liquid-tightly in the chamber, a push button attached to and adapted to actuate the piston and which is capable of being pressed by the patient a desired number of times corresponding to an amount of liquid medicine to be dosed, and a spring urging the piston towards its home position. After the patient presses the button and removes his hand from the button, the spring forces the piston backwards to its home position and the resulting negative pressure causes a subsequent smooth refilling of the chamber. The apparatus, which is a simple structure and can be manufactured at a low cost, can be employed in an integrated system for the self-dosing of the liquid medicine.

Nevertheless, the applicant has appreciated that there is still further scope for improvement of the dosing features in medicament delivery devices such as those described in the disclosure directed to an injector device for delivering an ophthalmic solution to a cornea of an eye. This device may include a base configured to contact part of the eye, and a needle connected to the base, wherein needle may deliver the ophthalmic solution to the cornea as was published in WO2011163574 A1.

One of the challenges is precisely dosing prefilled syringes when only a small amount of liquid is needed, for example in the microliter range. The herein presented disclosure can improve the accuracy of dosing small amounts.

SUMMARY

The present disclosure is applicable to a number of medical dosing devices, including a variety of ranges of dosing volumes especially when it comes to small amounts of liquids. Incorporating one or more haptic, acoustic and or visual end of dose delivery signal feedback mechanisms into these medical dosing devices can ensure that the user of the device will be notified of the beginning and or ending of the medicament delivery sequence.

It is an object of the present disclosure to provide highly precise dosing for a medical delivery device and the disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

A first aspect of the disclosure concerns a micro dosing device for delivering a metered dose of a therapeutic fluid comprising, a dosing unit comprising a dosing chamber, a distal connector unit at a distal end for fluidly connecting a medicament container to the dosing chamber, a proximal connector unit at a proximal end for fluidly connecting the dosing chamber to a medicament delivery member, and an activation mechanism, wherein the dosing chamber is configured to receive and therapeutic fluid; the micro dosing device comprises a dosing mechanism when triggered by the activation mechanism provides an exactly metered dose of fluid to be expelled by the medicament delivery member.

In one embodiment, the activation mechanism comprises a liquid-tight piston rod slidably fitted into a piston guide, having a predefined rod volume, when acted on, the piston moves into the dosing chamber, wherein the displacement volume of the piston rod defines the dose volume being expelled upon activation and displacement of the piston rod into the dosing chamber.

A second aspect of the embodiment is that the activation mechanism comprises an activation member and a dosing mechanism; wherein the activation mechanism extends radially from the dosing chamber, wherein an activation member is coupled to the piston rod and displaces the piston rod upon actioning the activation member by a user.

A further aspect of the embodiment is that the micro dosing device further comprises a first one-way valve arranged at the dosing chamber inlet and a second one-way valve, wherein the first and the second one-way valve are configured to regulate the fluid flow in one direction, minimizing backflow.

In one example the dosing mechanism is a circumferential stopping member and comprises a predefined perpendicular extension with respect to the longitudinal axis L, wherein the radial extension is defined by the radial extension of the piston guide such that the circumferential stopping member abuts the piston guide when displaced by the activation button.

A further aspect of the embodiment is that the predefined perpendicular extension is defined such that the displacement of the piston rod comes to a halt at a predefined travel distance, enabling a pre-defined displacement volume.

In one example of the embodiment the activation mechanism comprises one or more lateral arms extending respectively along a lateral side of the activation button, wherein the lateral arms comprise ledges at their terminal portion, configured to abut the edge of a respective recess of a corresponding lateral side of the dosing unit.

A further aspect describes a ledge which is in contact with the edge of the respective recess at an initial non activated state, and after activation and expelling of the predefined dose volume of fluid, the ledge is displaced further apart from the edge of the recess, such that a visual feedback indicates that the therapeutic fluid has been expelled.

According to another aspect, the circumferential stopping member is a modular element predefining the dosing volume to be expelled by the dosing unit.

In one example the micro dosing device comprises an audible feedback which is provided by the stopping member when coming to a halt and abutting the edge of the piston guide, then a clicking sound is emitted, indicating a user the end of dose.

According to a further aspect, the circumferential stopping member is an integral part of the activation mechanism, wherein the activation member and the stopping member are moulded as one piece.

According to a further aspect, in order to enable multiple doses of the therapeutic fluid, expelled by the micro dosing device, the activation mechanism further comprises a resilient member acting on the activation mechanism resetting the displacement of the dosing mechanism and the piston rod.

In one embodiment the distal connector unit at the distal end is an integral part of the dosing unit moulded as one piece.

In one embodiment the proximal connector unit at the proximal end comprises a portion which is an integral part of dosing unit moulded as one piece and comprises a part which can receive and securely hold a variety of connecting modules with different connector means.

The micro dosing device of any of the preceding examples, further comprising an adapter module for the distal connector unit, configured to be securely hold within the distal opening of the distal connector unit and providing connector means for the medicament container such that different diameters or locking mechanisms of the medicament container can be adapted to the micro dosing device.

A second aspect of the disclosure concerns a method for use and assembly of a micro dosing device according to any of the preceding claims comprising the steps of: mounting a medicament delivery member in a medicament delivery connector, being the proximal connector, at a proximal end of a dosing unit; mounting a medicament container into a medicament container connector, being the distal connector, at distal end of the dosing unit; activating the expelling mechanism of the medicament container; expelling the medicament fluid into the dosing unit; activating the activation mechanism by applying a force onto the activation member for expelling the metered volume of medicament at the medicament delivery member; wherein none of the steps are reversible.

Another aspect concerns a system comprising a micro dosing device according to one of above examples and a container comprising a liquid pharmaceutical preparation, wherein the container is connected to the distal connector.

System according to the preceding example, wherein the micro dosing device is preassembled on the container.

System according to the last two preceding examples wherein the container is a syringe comprising a liquid pharmaceutical preparation.

System according to the preceding example, wherein the syringe is a prefilled syringe.

The above described system, wherein the liquid pharmaceutical preparation is a protein, a fusion protein or an antibody.

According to a further aspect, the protein, the fusion protein or the antibody is a VEGF antagonist.

According to a further aspect of the above system, the liquid pharmaceutical preparation comprises aflibercept, ranibizumab or bevacizumab or a biosimilar thereof.

Another aspect concerns a kit comprising a micro dosing device as described above and a container comprising a liquid pharmaceutical preparation.

The kit as described above wherein the container is a pre-filled syringe comprising a liquid pharmaceutical preparation.

According to an alternative embodiment of the disclosure, the micro dosing device comprises an activation mechanism which further comprises a resilient member acting on the activation mechanism resetting the displacement of the dosing mechanism and the piston rod.

These and other aspects of and advantages with the present disclosure will become apparent from the following detailed description and from the accompanying drawings.

BRIEF DESCRIPTION OF THE DRAWINGS

Embodiments of the disclosure will now be described by way of example only and with reference to the accompanying drawings, in which:

FIG. 31A to FIG. 31C show the activation button of the embodiment of FIG. 14 from different perspectives and cross section.

FIG. 32A to FIG. 32C show alternative sealing means for the piston rod of the activation button.

FIG. 33A to FIG. 33D show alternative activation button and housing assemblies.

FIG. 34A to FIG. 34G show alternative security or integrity means.

DETAILED DESCRIPTION

Figure 1:
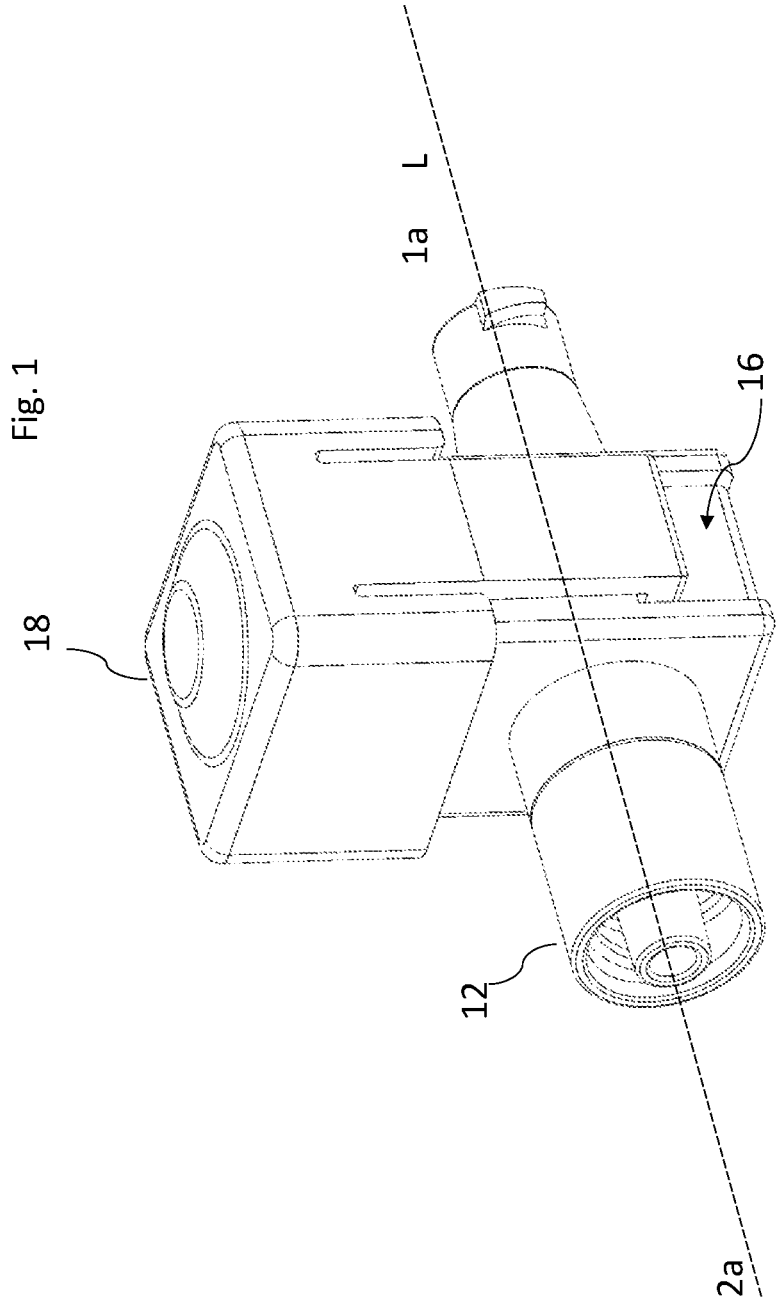
FIG. 1 shows a perspective side view of the medical micro dosing device.
Figure 3:
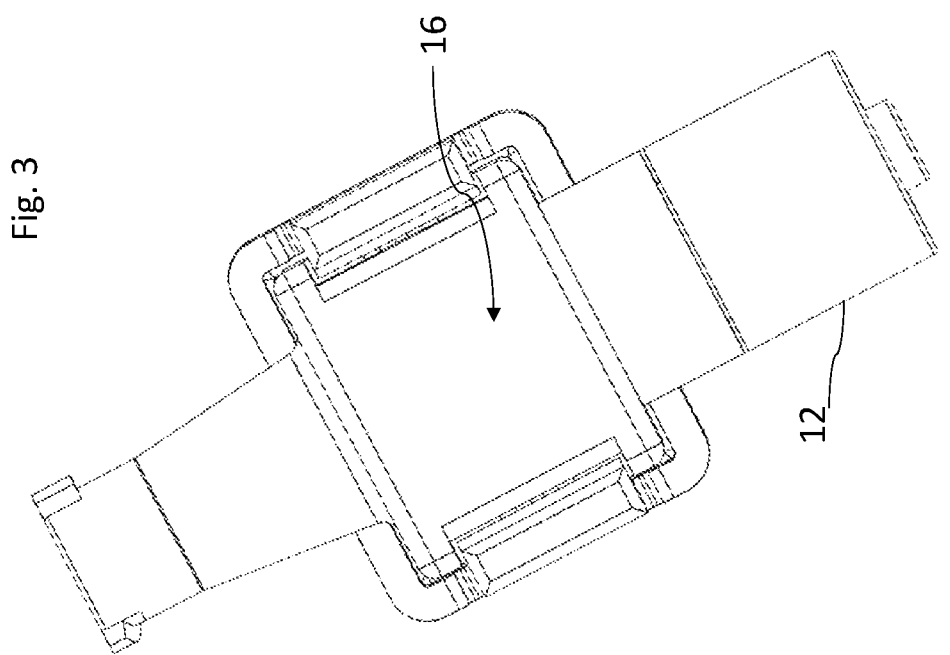
FIG. 3 shows a bottom view of the micro dosing device.
Figure 2:
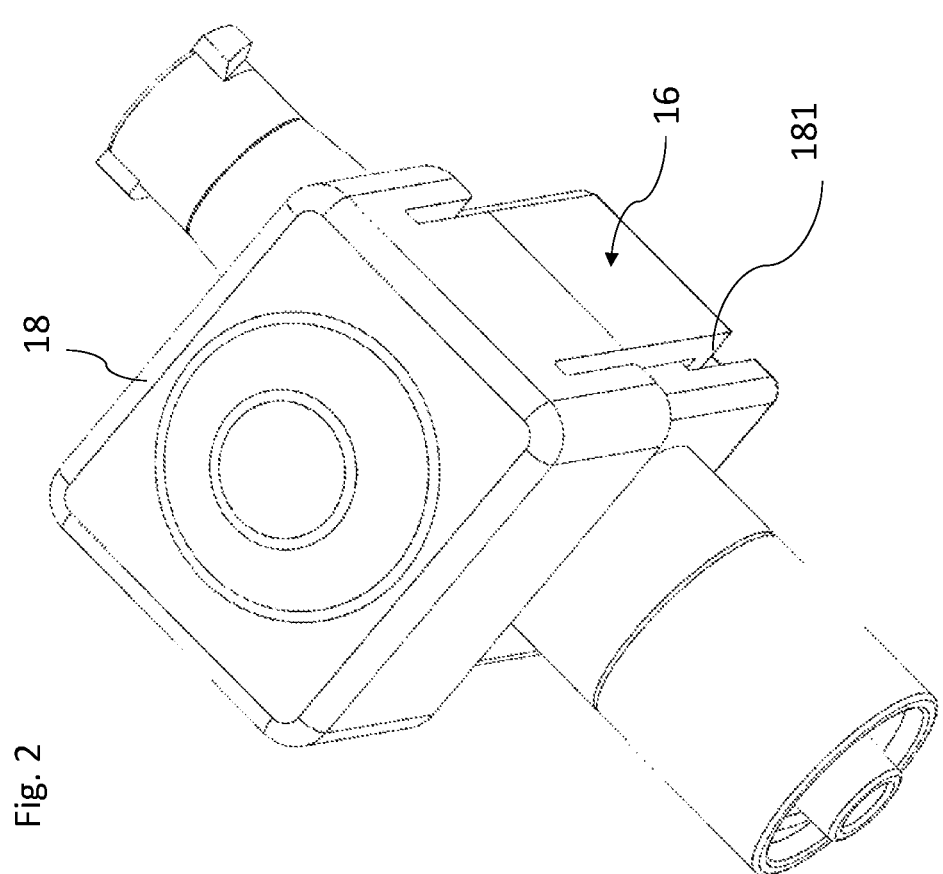
FIG. 2 depicts a perspective top view of the medical micro dosing device.

Various modifications to the embodiments described are possible and will occur to those skilled in the art without departing from the disclosure which is defined by the following claims.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the arrangements shown in the figures should not be viewed as limiting. It should be understood that other embodiments may include more or less of each element shown in a given figure. Further, some of the illustrated elements may be combined or omitted. Yet further, an example embodiment may include elements that are not illustrated in the figures.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, apparatus, element and method "configured to" perform a specified function is indeed capable of performing the specified function without any alteration, rather than merely having potential to perform the specified function after further modification. In other words, the apparatus, element, and method "configured to" perform a specified function is specifically selected, created, implemented, utilized, programmed, and/or designed for the purpose of performing the specified function. As used herein, "configured to" refers to existing characteristics of an apparatus, element, and method which enable the apparatus, element, and method to perform the specified function without further modification. For purposes of this disclosure, an apparatus, element, and method described as being "configured to" perform a particular function can additionally or alternatively be described as being "adapted to" and/or as being "operative to" perform that function.

Further, in the following description, the wording medicament delivery device will be used. In this context, medicament delivery devices may include a number of devices capable of delivering certain doses of medicament to a user. The medicament delivery devices may be of either disposable type or re-usable type and may be provided with medicament containers suitably arranged for specific drugs in specific forms.

Although the medical device described below is a medicament delivery device configured as a disposable single-use injector, any type of single dose medicament delivery device could incorporate the dosing mechanisms of the present disclosure, including, but not limited to, vaporizers, inhalers or eye dispensers. Likewise, the medical dosing device may be a training device that replicates a medical dosing delivery device.

In one embodiment, the medical micro dosing device 10 as described in more detail below has a dosing unit body 16, the dosing unit body having a proximal end 2 and a distal end 1. The dosing unit body 16 has a compact shape with a tubular member extending from the distal end 1 to the proximal end 2 along a longitudinal axis L, the dosing unit body having a distal opening 141 and a proximal opening 121. At a median position the tubular member defines a dosing chamber 163 having a perpendicular, relative to the longitudinal axis L, opening 167. An activation mechanism 18 and a dosing mechanism 182 are positioned within the perpendicular opening 167 of the dosing chamber 163 fluidly sealing the dosing chamber with sealing means 166. The activation mechanism and the dosing chamber together are of a compact shape, in this example a cubic shape. The activation mechanism 18 extends radially (i.e. perpendicularly) from the longitudinal axis L and is located adjacent to the dosing chamber 163 along the perpendicular axis.

The micro dosing device 10 comprises at its proximal end 2 a proximal connector unit 12 for a medicament delivery member, and at its distal end, a distal connector unit 14 for a medicament container not shown in the figures. The micro dosing device 10 is assembled with the dosing unit 16 arranged between the medicament delivery member connector unit 12 and the connector unit for the medicament container 14.

In one embodiment the proximal connector unit 12 is a modular unit mounted into the proximal opening of the dosing unit 16. This modular connector unit 12 may be reversibly or irreversibly connected with the proximal opening of the dosing unit, for example with threaded means or snap fit means or glued or welded connections allowing connection of a wider variety of medicament delivery elements to the dosing unit 16.

The micro dosing device 10 comprises a mechanism pre-configured to expel a precisely metered single dose of the fluid substance of the medicament container via the medicament delivery member.

The medicament delivery member (not shown here) is in fluidic communication with the dosing chamber via the medicament delivery member connector unit 12 wherein this proximal connector unit 12 comprises mounting and/or locking means, sealing means and means for fluid connection to the medicament container. The proximal connector unit 12 has a generally tubular body with a distal opening 141 and a proximal opening 170, and may be configured to securely receive, hold and seal the medicament delivery member. The medicament delivery member may comprise a needle or in an alternative embodiment any other appropriate element or method for medicament delivery, for example an aerosol dispenser or jet injector. The dosing chamber 16 fluidically connects the medicament delivery member to the medicament container via the medicament container connector unit, being the distal connector unit 14. In other words, the dosing unit 16 provides a fluid path between the medicament container and the medicament delivery member. The micro dosing device 10 may comprise one or more one-way valves 164 at the proximal ending of the connecting unit 14, thereby defining the dosing chamber inlet. The distal end of the connecting unit 14 defines the opening for introducing the medicament container.

In one embodiment the medicament container may comprise additionally an adapter module 142 such that a medicament container with a different securing or locking mechanism can be mounted on the distal connector unit 14.

The medicament container (also not shown here) is preferably a prefilled syringe but may be a cartridge, a mini bag or any other appropriate medicament storage unit. One advantage of the distal connector unit 14 is that the shape and size of the medicament container is not predefined by the shape of the housing.

In one embodiment the proximal connector unit 12 on the proximal end is an integral part of the dosing chamber 16 and is manufactured for example as a single piece. The distal connector unit 14 on the distal end may be either a modular unit or a molded unit.

In one embodiment the proximal connecting unit 12 comprises locking means for securely holding in place the connecting unit 12 when mounted on the dosing unit 16. Some examples for suitable locking means are conventional Luer-lock means, threaded means, snap fit means, bayonet threaded means, or magnetic securing means for example may be applicable. Another embodiment may comprise locking and securing means, for example means by laser welding, ultrasonic welding or any other suitable bonding means and methods.

When the medicament container is mounted on the distal connector unit 14, a therapeutic fluid can be expelled from the medicament container 14 via the one-way valve 164 into the dosing chamber 16. In this example, a one-way valve 164 provides a fluid communication with the dosing chamber and is further acting as a seal, as it is arranged to prevent fluid back flow from the dosing chamber 163 or the distal fluid guide 165 to the medicament container. The fluid is expelled upon actuation on an expelling mechanism of the medicament container, for example a plunger rod or any other suitable expelling mechanism for expelling the therapeutic fluid. The fluid exerts a force on the one-way valve 164 deforming the valve such that a fluid flow is enabled, letting the therapeutic fluid pass through the valve 164. The one-way valve covers and seals the proximal opening of the component 14, and a further seal like an O-ring may be used additionally for sealing purposes. The fluid can enter the dosing chamber 163 through this valve opening. Thus, the dosing chamber 163 comprises a fluid inlet on the distal side, being the fluid outlet of the one-way valve 164, a micro dosing cavity and a fluid passage 165 for guiding the fluid to the dosing chamber outlet 170 arranged at the connector 162 of the medicament delivery member 12. A second one-way valve 122 or alternatively a sealing member may be arranged after the dosing chamber outlet 170 in order to tightly seal the connection between the medicament delivery member 12 and the dosing unit 16, and to allow multiple doses, further preventing backflow from the proximal end 2.

Additionally or alternatively, a filter unit 120 may be placed before the medicament delivery member, for retaining possible crystalline or particle elements floating in the fluid.

One aim of the disclosure is to deliver a highly accurate dose of the medicament. Generally, the micro dosing mechanism is in fluid communication with the dosing chamber 16 and extends radially i.e. axially from the dosing chamber on a perpendicular axis with respect to the longitudinal axis L. The micro dosing mechanism comprises a piston rod 168 positioned in a piston guide 172, whereby the piston rod 168 extends into the dosing chamber 163 and is connected to an activation mechanism 18. In one embodiment the piston 168 fits tightly into the guide 172 such that no fluid can penetrate between the guide walls and the piston 168.

In one embodiment the piston rod 168 comprises a circular recess 169 configured to accommodate a sealing element, for example a circular sealing ring 166, which tightly seals the piston rod against the piston guide 172. The sealing member 166 prevents the therapeutic fluid from penetrating the space between the piston guide 172 and the piston 168. The piston rod 168 is further connected to the activation mechanism 18. In one example the activation mechanism is an activation button 180, and when a force applied by a user for initiating the dose delivery, the force is directly transferred onto the piston rod 168. The activation mechanism further comprises a stop mechanism 182 arranged to bring the piston displacement to a halt even if the force is still acting on the piston 168. The stop mechanism 182 is further configured to provide the exact dosing volume for the dosing mechanism.

One aspect of the micro dosing mechanism is that the piston rod displacement corresponds to a precise volume of the medicament to be delivered. In other words, the volume of the piston rod 168 extending and moving into the dosing chamber 163 under the applied force onto the activation button 180 displaces the equivalent amount of medicament volume to be expelled. In one embodiment the stop mechanism 182 has a precise height, such that a predefined piston displacement corresponds to the volume of the medical fluid dispelled out of the dosing chamber. Different heights of the stopping member 182 allow different volumes of medical fluid to be dispelled within the same dosing chamber. In other words, the distance travelled by the piston rod enables a predefined displacement volume, which depends on the height i.e. radial extension of the circumferential stopping member 182.

Figure 6:
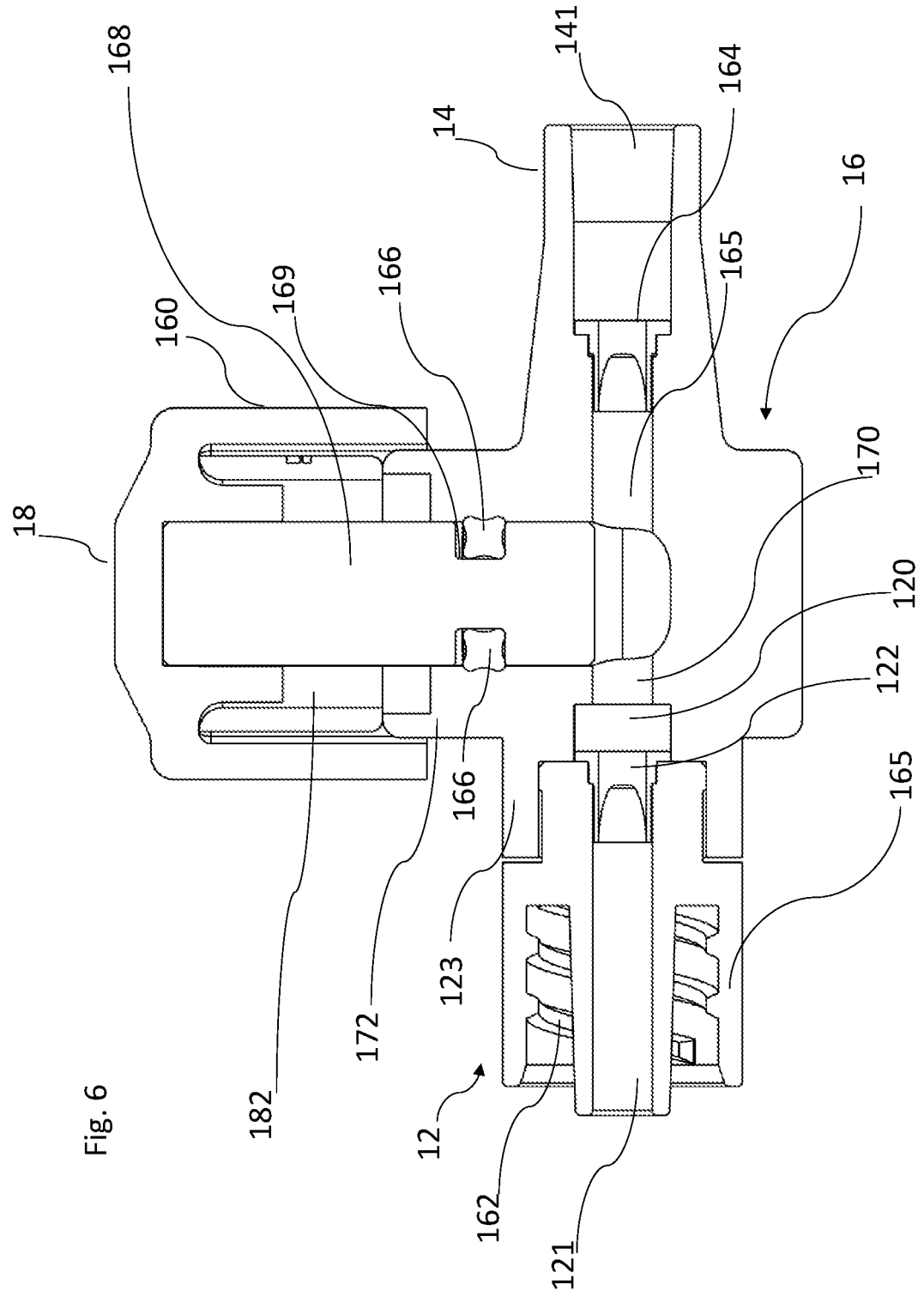
FIG. 6 shows a cross sectional view of the micro dosing device.
Figure 7:
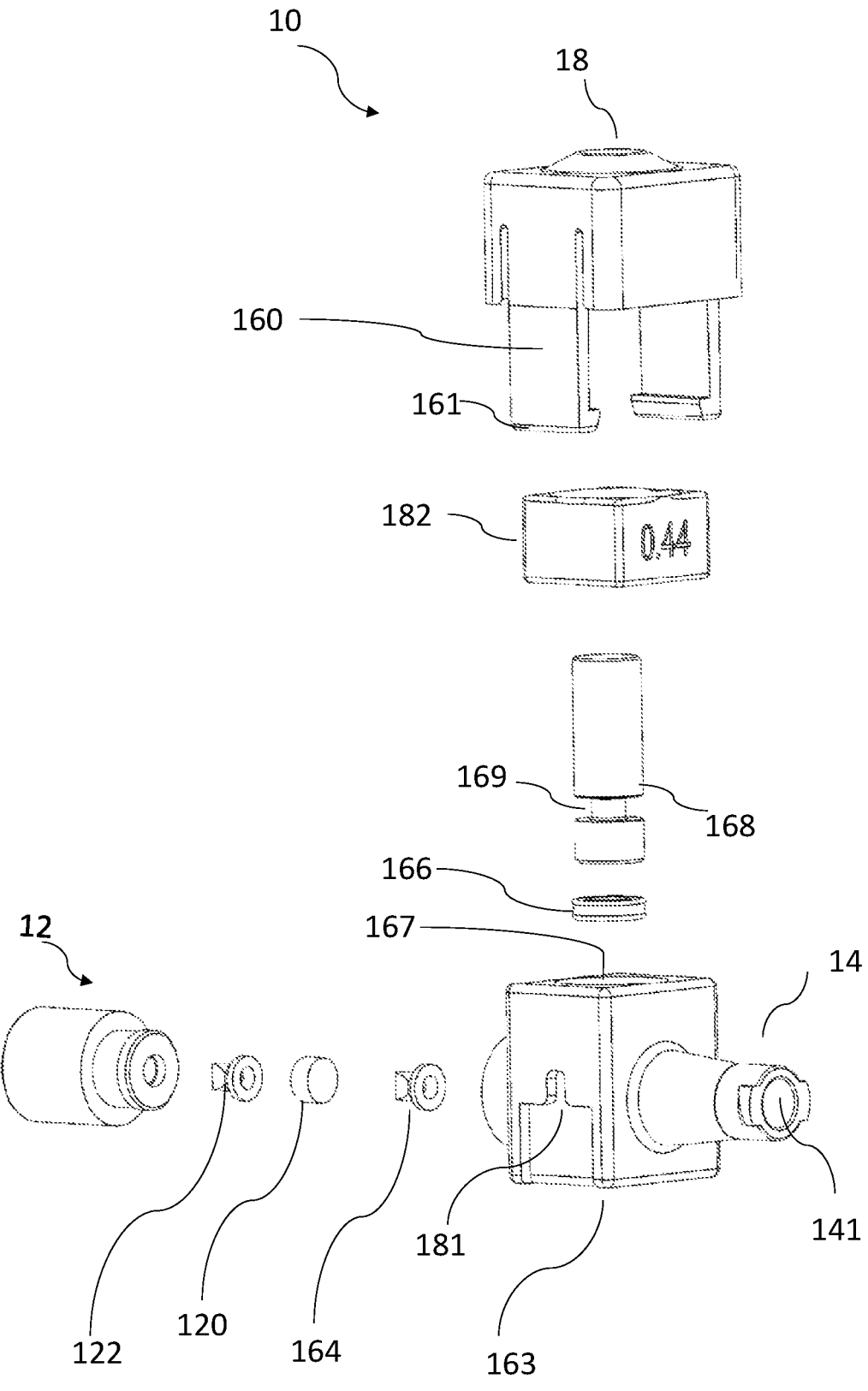
FIG. 7 shows a fully exploded view of the micro dosing device.

As shown in the cross-sectional view in FIG. 6, the activation mechanism covers the perpendicular opening 167 of the dosing chamber 163, providing an activation button 180 on the outer surface of the activation mechanism 18. Below the activation button 180 a recess for the piston rod is configured to receive and securely hold the piston rod attached to the activation mechanism.

The activation mechanism further comprises a circumferential opening or recess configured to accommodate the stopping member 182. The stopping member 182 has the same circumferential shape and extension as the piston guide and is configured to abut the edge of the piston guide 172. The activation mechanism 18 further comprises lateral arms 160 extending along lateral sides of the activation button 180, comprising ledges 161 at the terminal section, configured to abut the edge of a respective recess 181 at the corresponding lateral sides of the dosing unit 16. The activation button thus is securely held in an initial position and may not be pulled away or be disengaged from the activation mechanism.

In one embodiment the activation mechanism, the cover element with the activation button 180 and the piston rod 168 are an integral element, for example molded as one piece.

In another embodiment the activation mechanism, i.e. the cover element with the activation button 180, the piston rod 168, and the stopping mechanism 182 are an integral element, for example molded as one piece.

Figure 8:
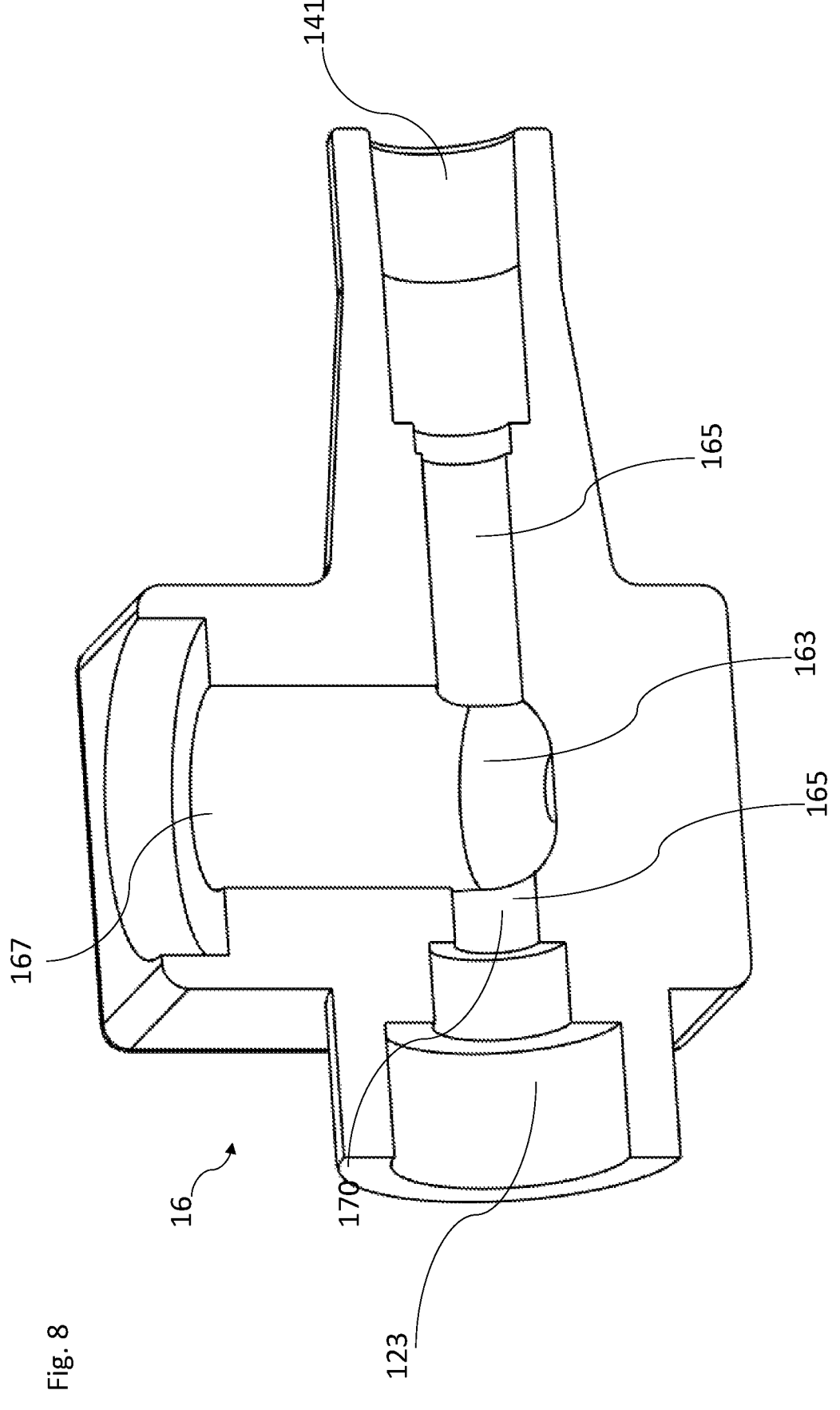
FIG. 8 shows a cross sectional view of the integral unit of the dosing chamber as moulded.

As shown in FIG. 8 the dosing chamber unit 16 of this example is molded as one piece or, alternatively, the dosing chamber may be of a modular type assembled in an air and liquid tight manner. For example, it may be glued or welded together.

Figure 4:
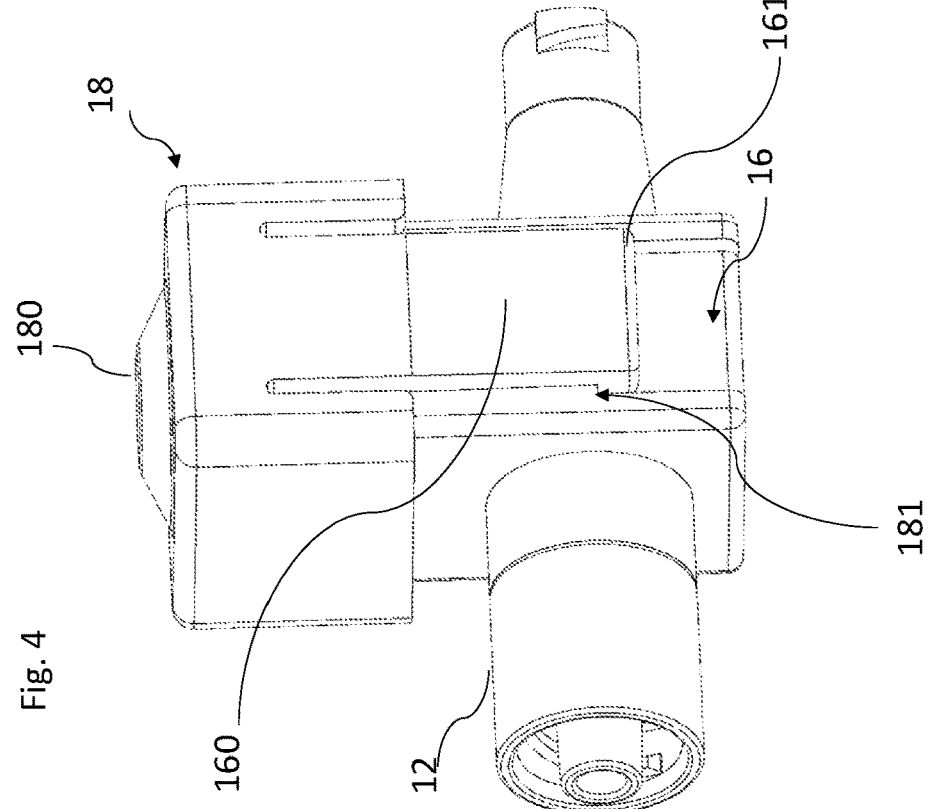
FIG. 4 shows a perspective view of the micro dosing device before use.

The initial state of the micro dosing device is shown in FIG. 4. The activation mechanism (i.e. the activation button 180) has not been pushed by a user and the lateral arms 160 with the ledges 161 are in an initial position, abutting the edge of the recesses 181 on the side wall of the dosing unit 16.

Figure 5:
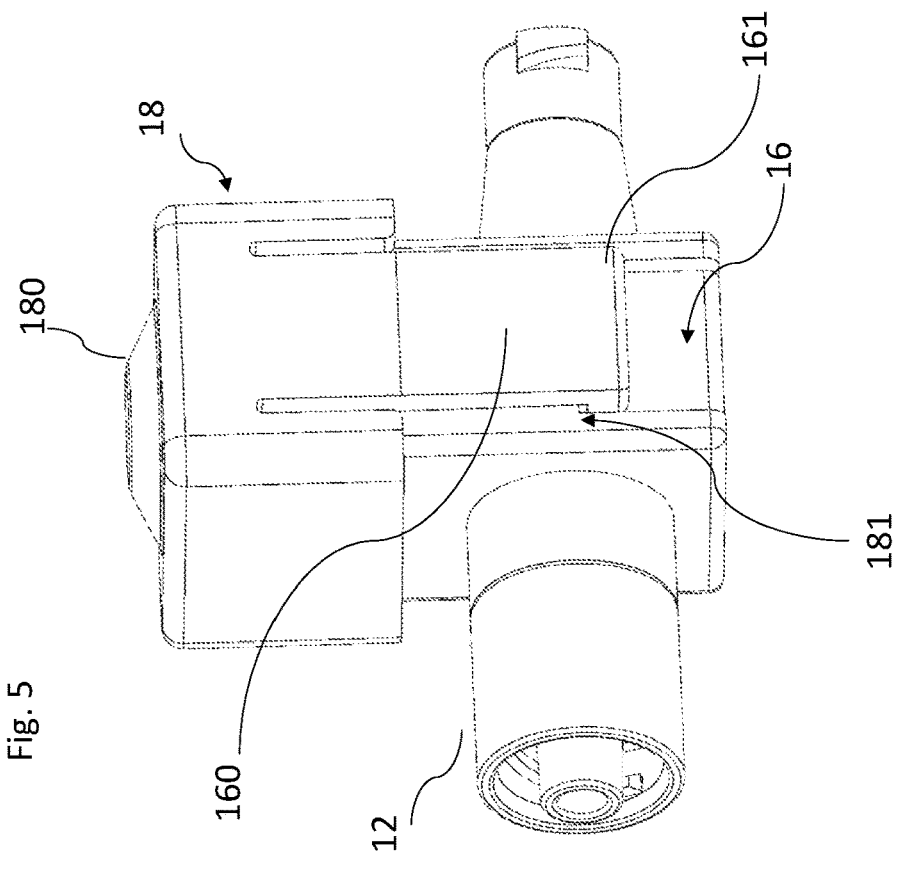
FIG. 5 shows a perspective view of the micro dosing device after use i.e. after expelling of the micro dose of the medicament.

After activation, or in a final state, the micro dosing device is shown in FIG. 5, whereby the activation mechanism i.e. the activation button 180 has been pushed by a user and the lateral arms 160 with the ledges 161 moved to a final position, leaving a space between the recesses 181 on the side wall of the dosing unit 16 and the ledge 161. This is a visual indicator that the dosing device has been used or actuated.

In the final state, when the exact amount of medicament dose volume has been expelled, the activation button 180 is stopped by the stopping mechanism 182. The stopping mechanism may for example be a structural stopper, like a layer or protrusion. In one example, the stopping mechanism is a circumferential element attached to the activation mechanism and it is displaceable with the activation mechanism upon activation until it abuts the edge of the piston guide and thus stops the displacement of the activation mechanism and the piston.

The stopping mechanism may further comprise haptic and/or acoustic feedback, i.e. when the circumferential element abuts the edge of the piston guide the user may hear a clicking sound and feel opposing force.

It will be appreciated that the one-way valve 164 will be understood as a non-return valve permitting a fluid passage in one direction only, not allowing the fluid passage in the opposite direction. One alternative example to a valve may be a septum needle fluidly connecting the medicament container with the dosing unit.

The dosing unit 16 comprises a dosing chamber 163, a micro dosing mechanism and an activation mechanism 18. The dosing unit 16 is in fluid communication with the medicament delivery member via the proximal connector 12 at the proximal end 2 of the dosing unit 16, onto which the medicament delivery unit may be mounted via releasable securing means for example Luer-lock connectors or any other threaded, snap fit or other suitable connecting means.

In one embodiment the micro dosing device 10 is configured for a single use and to provide a single dose after which the activation mechanism may be reversibly or irreversibly locked.

In an alternative embodiment, the micro dosing device 10 may be configured for multiple dose deliveries. In this example the activation mechanism may comprise a resilient member instead of the locking means 182, such that after a first dose delivery the activation mechanism may be reset to the initial position, allowing subsequent dose deliveries. In this example the medicament container is chosen to provide the required amount of subsequent dosages.

The method for assembly and uses of the micro dose delivery device 10 comprises the step of mounting the medicament container on the distal connector unit 14 at the distal end 1 of the device 10. In one embodiment the distal connector unit 14 comprises threaded means such that the medicament container is mounted on the distal connector unit 14 by a turning movement of the user if a releasable threaded lock mechanism is used. Alternatively, the connector adapter 142 may be used to adapt the locking mechanism of the medicament container to the locking means of the dosing unit 16, and then mounted onto the dosing unit 16. Then the medicament delivery member is mounted on the connector 162 at the proximal side 2 of the dosing unit 16. The sequence or order of the above steps may be reversed. When the medicament delivery member and the medicament container are securely mounted on the connectors 162, 141 of the dosing unit 16, a fluid connection between the medicament container and the medicament delivery member via the dosing chamber 163 of the dosing unit 16 is established.

Subsequently, the medicament container is actuated by the user to dispense the medicament into the dosing chamber 163 until the medical fluid reaches the medicament delivery member. Thereby all fluid flushes through the available spaces until the entire volume is filled with the therapeutic fluid. In other words, the dosing chamber 163, the fluid guides 165, the dosing chamber outlet 170 and the medicament delivery member outlet, for example a needle, are all filled with the fluid. Accordingly, all subsequent fluid displacement does not depend on the needle volume, the fluid guide or the outlet volume.

It is to be understood that the assembly of the micro dosing device 10 is generally performed under medical usual antiseptic or sterile medical procedures or under sterile conditions.

One advantage is that different needle sizes with different needle volumes may be used without adapting the dosing mechanism to the needle size. Another advantage is that potential air pockets or bubbles are more easily expelled at the medicament delivery member outlet.

Once the micro dosing device 10 is assembled as outlined above, the medicament can be expelled as an exact dose volume when the user actuates the micro dosing mechanism by pushing on the activation button 180.

One advantage of the modular structure of the micro dosing device 10 is that with the same dosing unit 16 and the same activation mechanism 18, the dosing mechanism can be easily adapted to any dosing volume which may be chosen within a specific dosing volume range. The available range depends on the volume of the dosing chamber 163 and the available penetration volume of the piston rod 168. Accordingly, the same modular elements and set-up can be assembled with different stopping members 182. The respective heights, or axial extension of the stopping member 182 determines the pre-set dosing volume. This allows for fewer parts for assembly, thus enabling lower costs and reduction of potential assembly errors.

Figure 15A:
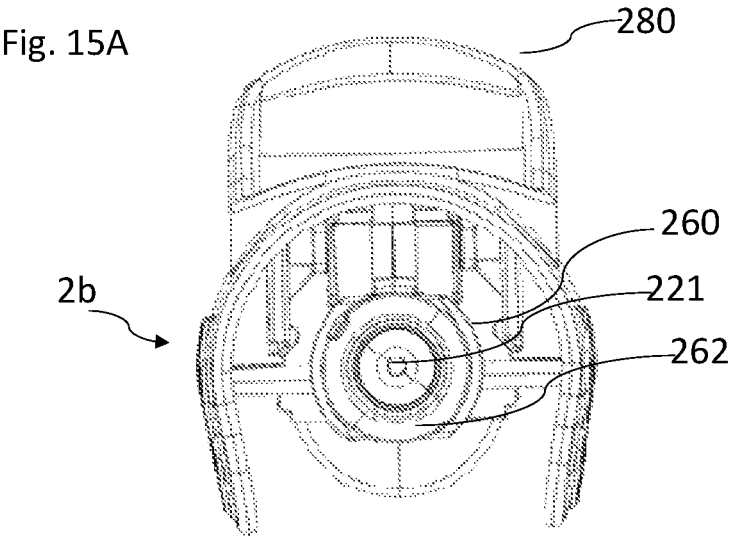
FIG. 15A shows the proximal front side of the device of FIG. 14.
Figure 15B:
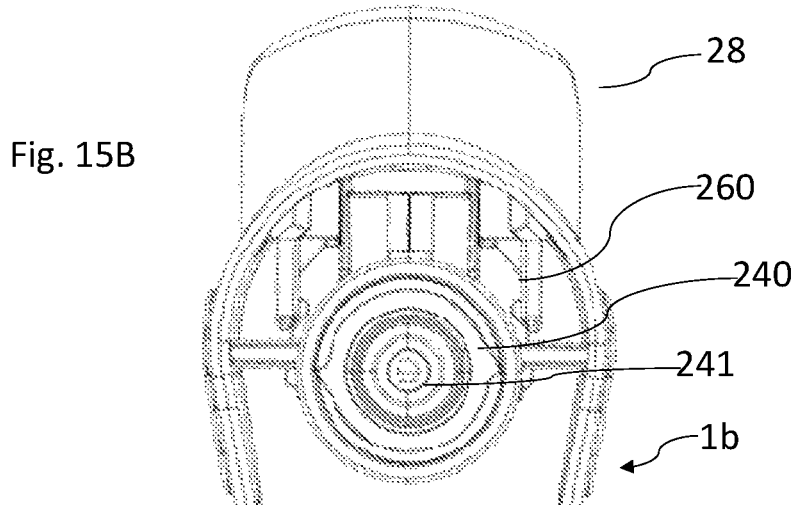
FIG. 15B shows the distal rear side of the micro dosing device of FIG. 14.
Figure 15C:
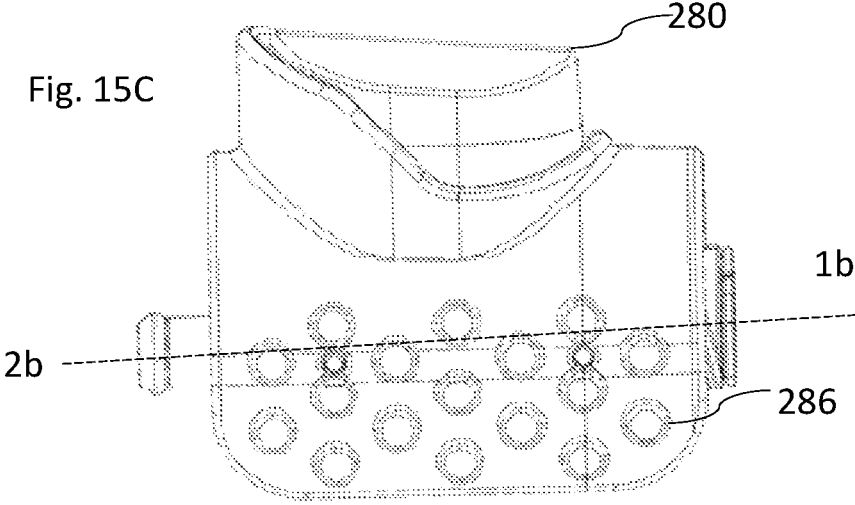
FIG. 15C shows a side view of the micro dosing device of FIG. 14.

In another embodiment illustrated in FIGS. 9 to 31, the medical micro dosing device 20 as described in more detail below has a dosing unit body 26, the dosing unit body having a proximal end 2b and a distal end 1b as shown in FIG. 15C. The dosing unit body 26 comprises a tubular member extending from the distal end 1b to the proximal end 2b along a longitudinal axis L, the dosing unit body comprising a connector valve adapter 241 in a distal opening of the dosing unit body, and comprising a medicament delivery outlet 221 in a proximal opening of the dosing unit body. At a position between the medicament delivery member connector unit 22, being the distal connector unit 22, and the proximal connector unit for the medicament container 29, the tubular member defines a dosing chamber 263 having a perpendicular, with respect to the longitudinal axis L, opening 267. An activation mechanism 28 and a dosing mechanism are positioned within the perpendicular opening 267 of the dosing chamber 263. Further, in the opening 267 is arranged a piston guide 272 configured to receive the piston rod 268 and sealing elements 266, the sealing elements are fluidly sealing the dosing chamber, wherein the sealing elements 266 are arranged between the inner surface of the piston guide 272 and the piston rod 268. The activation mechanism and the dosing chamber together are of a compact shape. The activation mechanism 28 is located adjacent to the dosing chamber 263 and extends radially (i.e. perpendicularly) from longitudinal axis L. An advantage of this design is that it can provide a compact dose unit body, thereby minimizing dead zones.

Figures 9, 10:
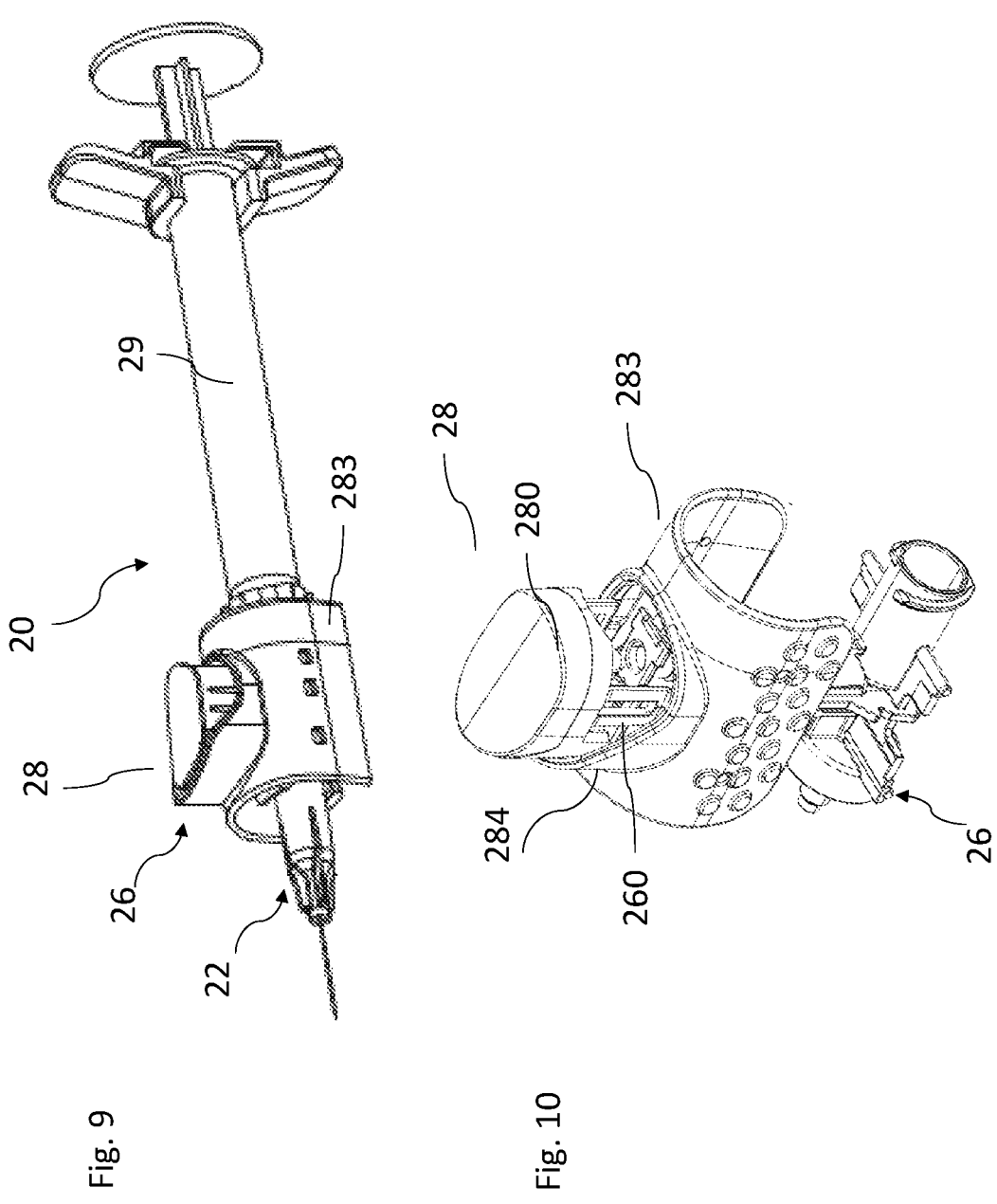
FIG. 9 shows a perspective side view of another embodiment of the micro dosing device ready to use with a syringe and a needle.
FIG. 10 shows a fully exploded view of the micro dosing device of FIG. 9 without syringe and needle.

The micro dosing device 20 comprises at its proximal end 2b a proximal connector unit 22 for a medicament delivery member, and at its distal end, a distal connector unit 24 for a medicament container 29. As shown in FIG. 9, the micro dosing device 20 is assembled with the dosing unit 26 arranged between the proximal medicament delivery member connector unit 22 and the distal connector unit for the medicament container 29, wherein the dosing unit 26 is connected to the distal connector 262 at the distal end and to the proximal connector 240 at the proximal end. The micro dosing device 20 further comprises an activation mechanism 28 extending radially (i.e perpendicularly) relative to the longitudinal axis L from the micro dosing unit 26.

The micro dosing unit 26 comprises a mechanism configured to expel a precisely metered single dose of the medicament of the medicament container 29 via the medicament delivery member 224.

The medicament delivery member 224 may comprise a needle 225 or in an alternative embodiment any other appropriate element or method for medicament delivery, for example an aerosol dispenser or jet injector.

The medicament container 29 is preferably a prefilled syringe and may be a cartridge, a mini bag or any other appropriate medicament storage unit. The micro dosing device 20 comprises a distal connector 240 on the distal end 1b of the dosing unit 26 and a proximal connector 262 on the proximal end 2b of the dosing unit 26.

In one embodiment the proximal connector 262 on the proximal end is an integrated part of the dosing chamber 26 manufactured for example as a single piece. The distal connector 240 at the distal end may comprise a modular unit 241.

In one example the proximal connector 262 is a modular unit mounted into the proximal opening of the dosing unit 26. This modular connector unit may be reversibly or irreversibly connected with the proximal opening of the dosing unit 26, for example with threaded elements or snap fit elements or having glued or welded connections allowing connection of a wider variety of medicament delivery elements to the dosing unit 26.

Figure 11:
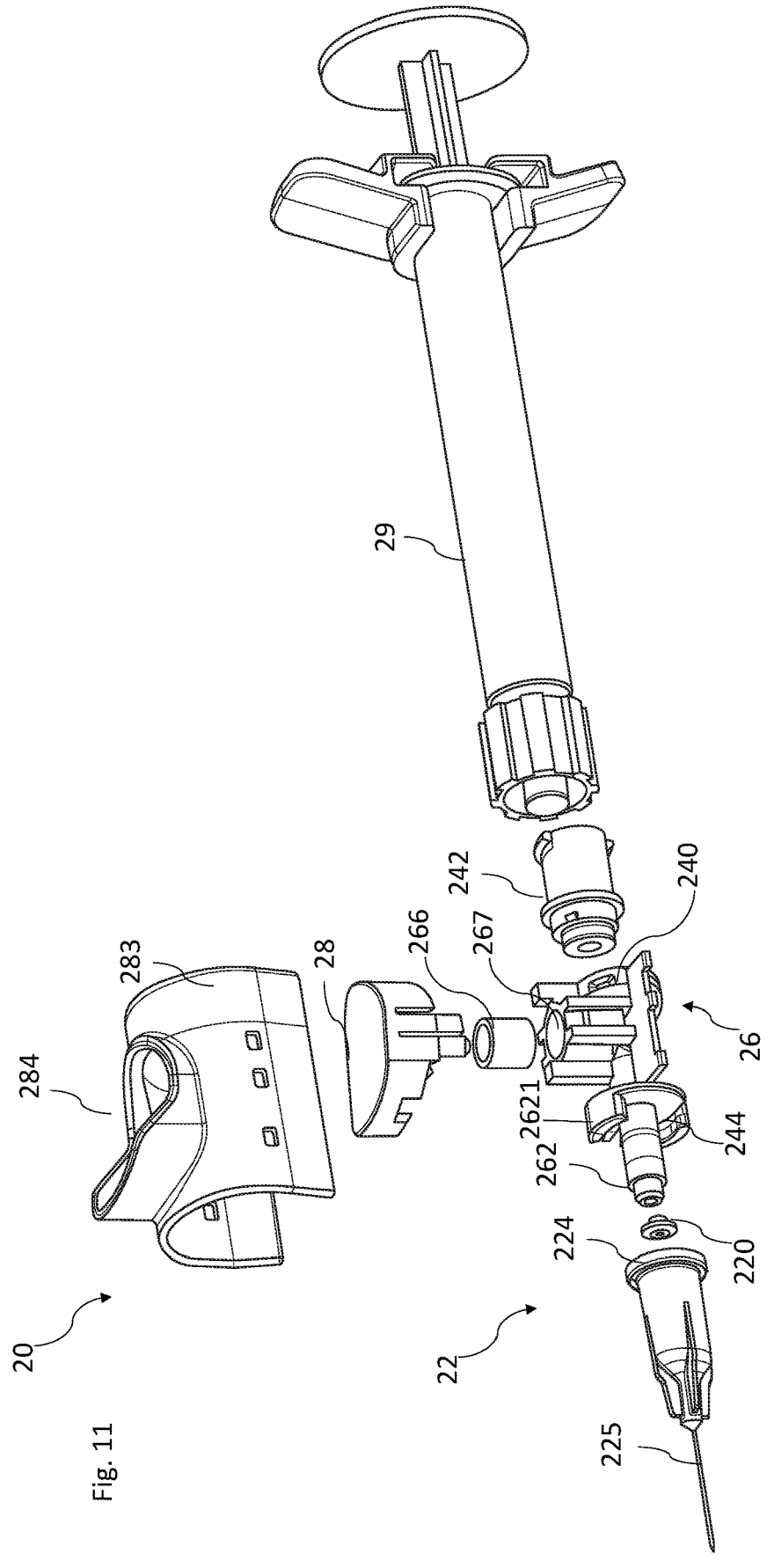
FIG. 11 shows a fully exploded view of the micro dosing device of FIG. 9 with syringe and needle.
Figures 12, 13, 14:
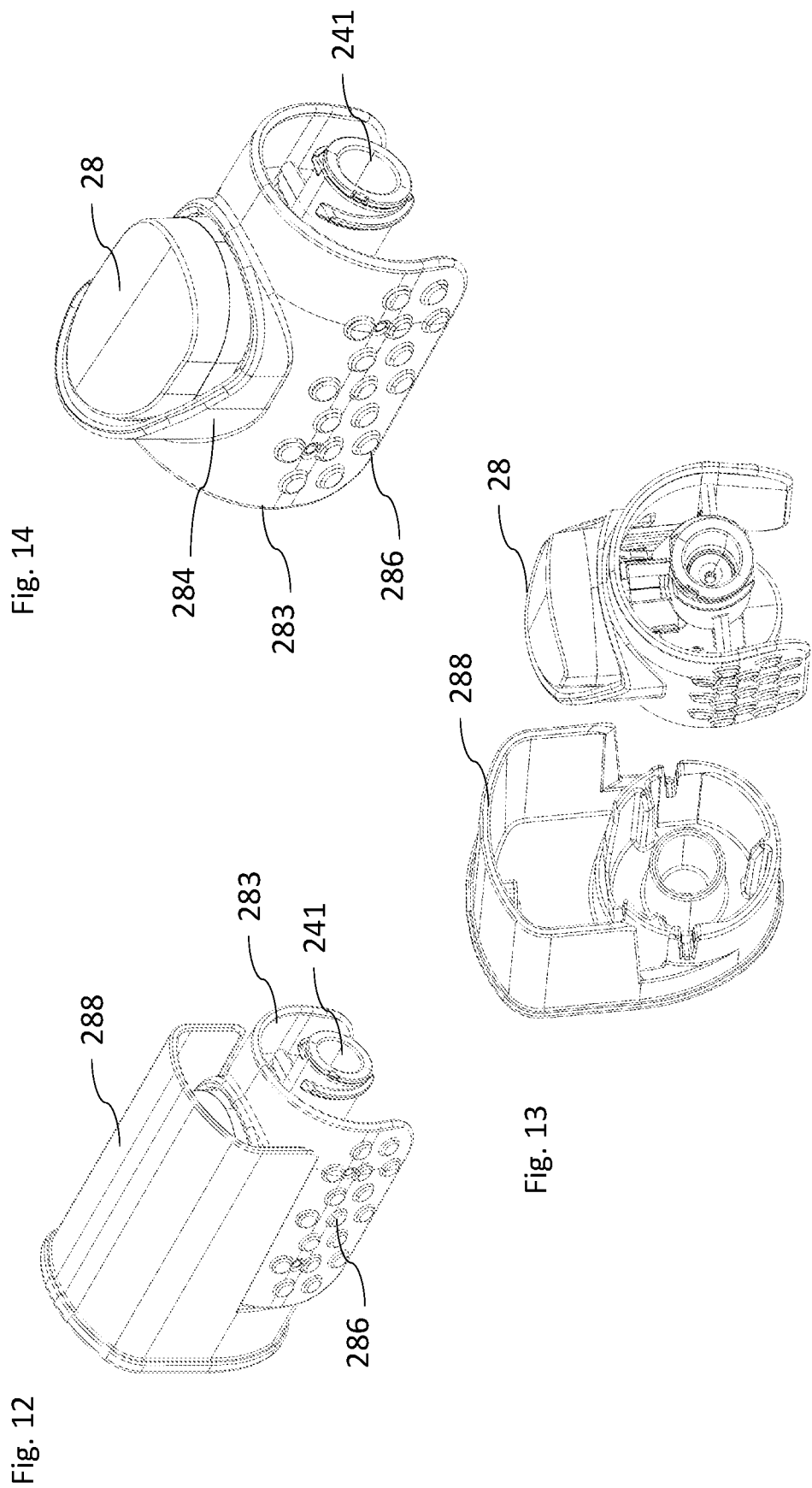
FIG. 12 shows a perspective view of the micro dosing device of FIG. 9 with a protective cover.
FIG. 13 shows an exploded view of the micro dosing device of FIG. 12 with the protective cover.
FIG. 14 shows a perspective view of the micro dosing device of FIG. 9 without the protective cover.

FIG. 11 shows the distal connector 240, onto which a medicament container 29 is mounted, wherein the distal connector 240 comprises mounting and/or locking elements, sealing elements and elements for a fluid connection to the medicament container. In one embodiment the distal connector 240 may comprise a component 241, wherein the valve adapter 241 is configured to be mounted on the distal end of the dosing chamber 263. The valve adapter 241 has a generally tubular body with a distal and proximal opening, and may be configured to securely receive, hold and seal the medicament delivery container 29. Further, the valve adapter 241 comprises a one-way valve 264 at the proximal end of the valve adapter 241, with the one-way valve 264 defining the dosing chamber inlet. The distal end of the valve adapter defines the opening for introducing the medicament container 29.

In one embodiment the valve adapter 241 comprises locking elements for securely holding in place the valve adapter when mounted on the dosing chamber 263, for example threaded elements snap fit elements, bayonet threaded elements, and/or magnetic securing elements may be applicable. Another embodiment optionally comprises locking and securing elements, for example by laser welding, ultrasonic welding or any other suitable bonding means and methods.

Figure 27:
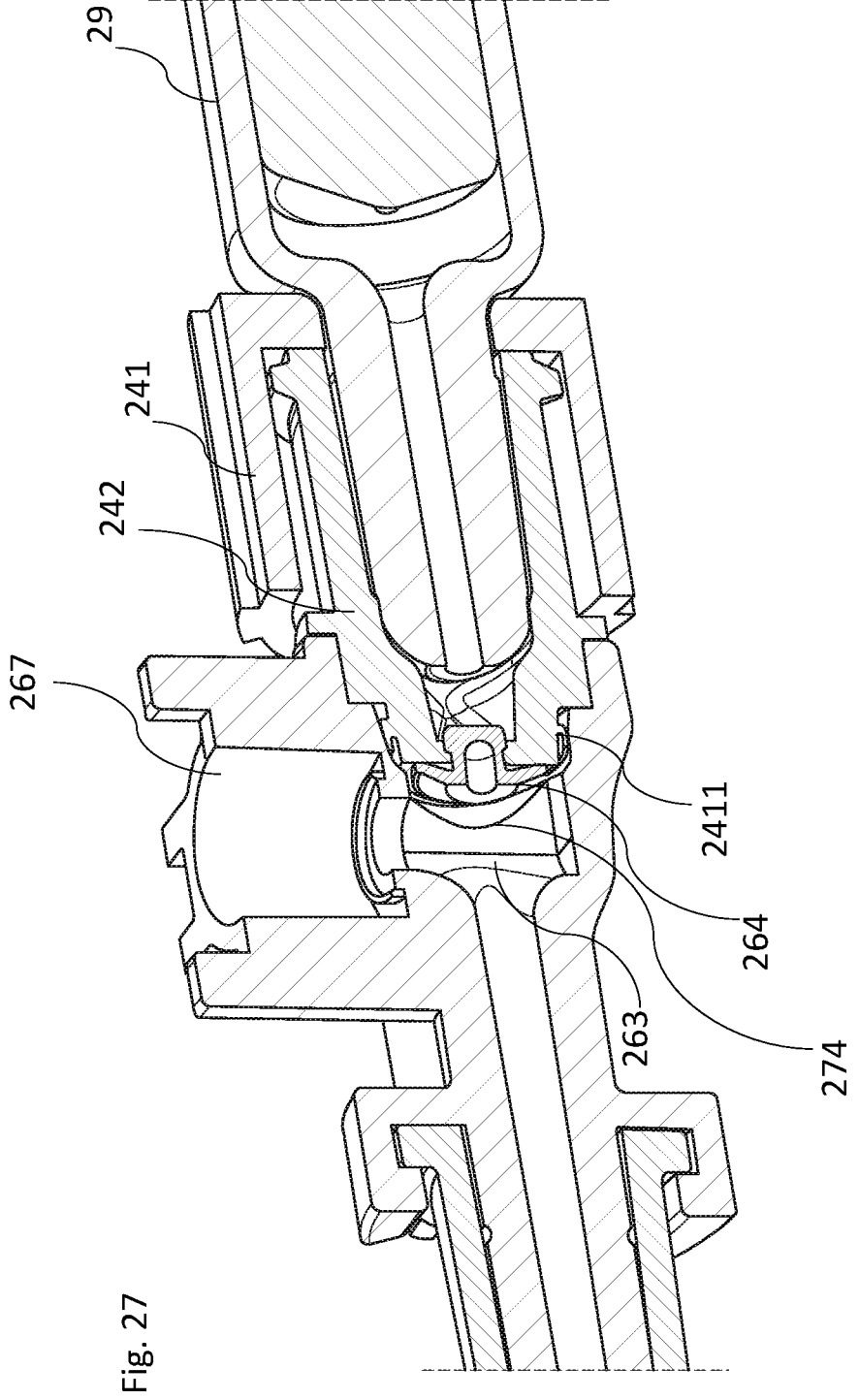
FIG. 27 shows a perspective view of the cross section of the embodiment of FIG. 22 with a syringe with a needle mounted on the device.

In one example the valve adapter 241 comprises wedge-shaped protrusions 2411 which, when introduced into dosing chamber 263, may engage with corresponding recesses on the inner surface of the distal end opening of the dosing chamber 263. As illustrated in FIG. 27, the wedge-shaped protrusions 2411 can flex into the recesses and securely hold valve adapter 241 securely in place.

When the medicament container 29 is mounted on the distal connector 240, a therapeutic fluid can be expelled from the medicament container 29 via the one-way valve into the dosing chamber 263. In this example, the one-way valve 264 defines a fluid communication with the dosing chamber and is further acting as a seal. The fluid is expelled by an expelling mechanism of the medicament container, for example by a plunger or any other suitable expelling mechanism for expelling the therapeutic fluid. The fluid exerting a force on the one-way valve displaces or deforms the valve such that a circular opening is created between the terminal section of the valve adapter 241 and the valve 264, thereby covering the proximal opening of the valve adapter 241. The therapeutic fluid can enter the dosing chamber 263 through the circular opening created by the valve deformation.

Figures 28A, 28B, 28C, 28D, 28E, 28F:
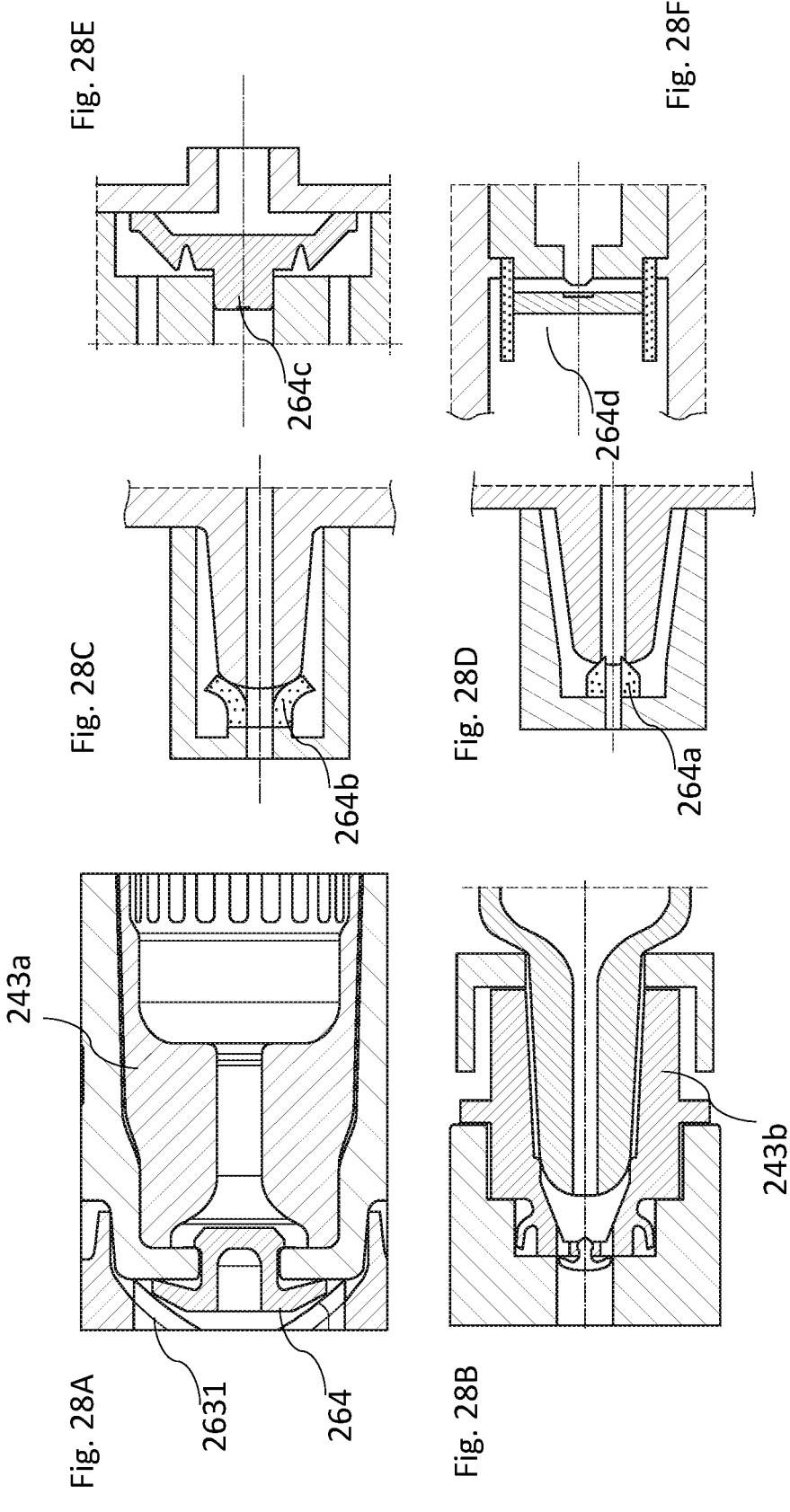
FIG. 28A to FIG. 28F show alternative distal connecting and inlet means.

In some embodiments, a space may be defined between the medicament delivery outlet and the valve surface directed towards the medicament delivery container. Optionally the shape and geometry of these side walls 2631 can be adapted or modified to minimize the space volume and to optimize the fluid flow characteristics, as shown in FIG. 28A. For example, a streamlined form of the sidewalls of said defined space may improve the fluid flow and reduce turbulence within the flow path of the fluid. Further, the inner sidewalls 2631 of the valve adapter 241 in some examples are configured to improve the gripping and locking of the medicament container within the distal opening of the valve adapter 241. For example, as shown in FIG. 28A the inner side walls may have a tapering shape or may have different thicknesses at some sections as shown in FIG. 28B.

Alternative one-way valve and side walls shapes are shown in FIG. 28A to 28F. Not shown in the Fig. but equally applicable for this purpose are duckbill valves and cross slit valves. FIG. 28B shows an inclined side wall, the inclined side wall comprising a slope decreasing from an outer position towards the longitudinal axis L in direction to the dosing chamber 263, thereby decreasing the diameter of the opening to the dosing chamber. FIG. 28B illustrates the distal connector 240 comprising the side wall 2631, the side wall comprising a step profile. FIG. 28D shows an alternative valve for the dosing chamber inlet, namely a front cone valve 264a. In FIG. 28C an inverted front cone valve 264b is shown. Another example is a Belleville valve 264c as illustrated in FIG. 28e. A bicycle hose type valve 264d as illustrated in FIG. 28F is an alternative example for a suitable valve for the dosing chamber inlet.

It will be appreciated that the one-way valve 264 will be understood as a non-return valve permitting a fluid passage in one direction only and not allowing the fluid passage in the opposite direction. One alternative example to a valve may be a septum needle fluidly connecting the medicament container with the dosing unit.

The one way-valve 264 further is configured to reduce the dead volume of the dosing chamber 263. The dead volume shall be understood as the free spaces created between connections. For example, the 3-dimensional shape and or size of the one-way valve 264 may also be optimized to tightly fit and to reduce spacing between the one-way valve 264 and the valve adapter 241. Accordingly, the one-way valve may be formed to fill out the space of the connecting parts and to improve fluid flow characteristics.

In one example the proximal connector unit 262 may comprise locking means 2621 for further tightening the locking engagement of the medicament delivery member 22 with the connector unit for further reducing dead volumes. One advantage is that in those cases where the medicament delivery outlet 22, for example the needle 225 or a needle holder, has a certain movement and fitting tolerance, the tolerance may be reduced or compensated with tightening elements such as O-rings, snap fits or Luer-locks, for example.

The locking and securing elements of connector unit 262, 240 for the medicament delivery member 22 and for the medicament container 29 are for example conventional Luer-lock type connectors, but any other suitable connector type is suitable; for example, the connector unit may comprise a threaded connector, a snap fit and/or a magnetic locking mechanism. The connector unit 240 for the medicament container optionally comprises an adapter module 242 such that when a medicament container 29 has a different securing or locking mechanism than the connector unit 240, the medicament container 29 can be mounted on the connector unit 240 via the adapter module 242. The adapter module is mounted on the medicament container 29 such that the medicament container can be mounted on the connector unit 240 with the adapter module attached.

The dosing unit 26 further comprises a housing 283 enclosing a dosing chamber 263, a micro dosing mechanism and an activation mechanism 28. The dosing unit 26 is in fluid communication with the medicament delivery member 22 at the proximal end 2b of the dosing unit 26. The medicament delivery member 22 is connected to the dosing unit 26 via the proximal connector unit 262, onto which the medicament delivery unit 22 is releasably mounted via securing and locking elements, for example Luer-lock connectors or any other threaded, snap fit or other suitable connector elements.

The dosing chamber 263 of the dosing unit 26 is arranged between the medicament delivery connecting unit 262 and the medicament container connecting unit 240. The dosing chamber 263 defines a precise volume and shape to optimize fluid flow of the specific therapeutic fluid. One example is that the inner walls of the dosing chamber adopt a specific shape such that when the fluid enters the dosing chamber, the flow of the fluid is guided by the inner walls of the dosing chamber such that the fluid flow is facilitated. For example, the specific 3-dimensional shape of the inner walls of the dosing chamber provides better adherence of the fluid to the sidewalls, which inhibits creation of air bubbles or pockets during the flushing process.

One aim of the disclosure is to deliver a highly accurate dose of the medicament; thus, leakage or backflow of the medicament has to be minimised or prevented. One aspect of the disclosure is to optimize the fluid flow mechanism. The dosing chamber is preferably rigid and comprises a streamlined 3-dimensional form 274 providing optimization of the fluid passage from the dosing chamber 26 to the medicament delivery member 22.

Figure 18:
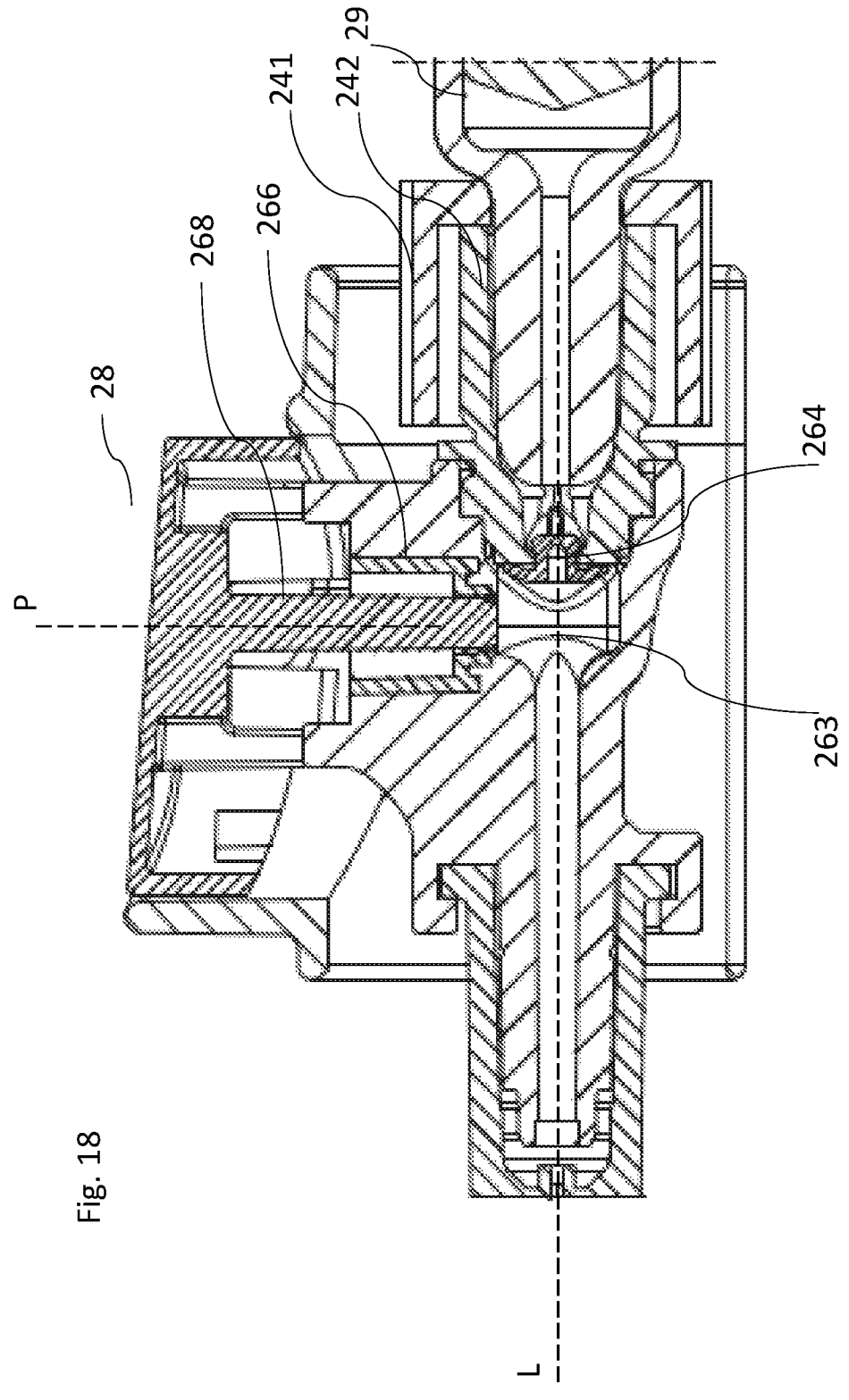
FIG. 18 is a cross sectional view of the device in FIG. 14.
Figure 20:
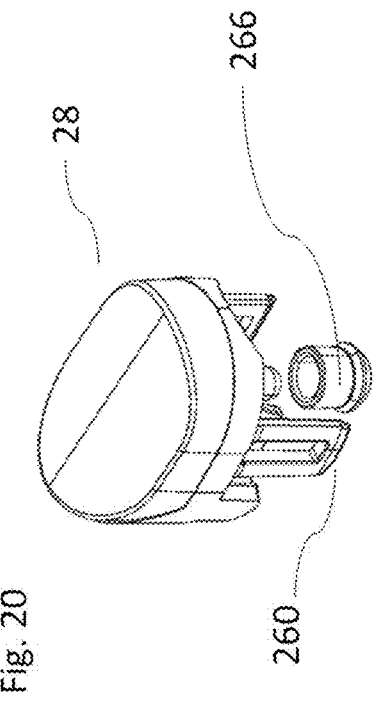
FIG. 20 shows an exploded view of the of the embodiment of FIG. 19.

In one example shown in FIGS. 18 and 27, the alignment of the central axis of the medicament container 29, is in line with the dosing chamber inlet 240 and the dosing chamber outlet with the medicament delivery member 225. This alignment supports a linear fluid flow path.

In one example the valve 264 is arranged such that it is symmetrically positioned about the longitudinal axis L, i.e. the centre of the valve is on the longitudinal axis L.

In one example, the valve comprises a central protrusion. The connector module 243 comprises a central hole, and the central protrusion of the valve is held in the central hole. The central protrusion extends in the distal direction from the center of the valve. A proximal side of the central protrusion comprises a central opening. The protrusion can be compressed to fit into the central hole of the connector module 243. When the protrusion expands back out in the central hole of the connector module 243, the one-way valve 264 is held securely in place. The connector module 243 further comprises at least one additional opening adjacent to the central hole, which is sufficiently small not to affect the holding mechanism of the valve 264 but sufficiently large to improve the fluid flow through the valve 264. In this example, due to the coaxial arrangement of the valve and the central hole in the connector module, the fluid enters the dosing chamber 263 through a ring-shaped space around the valve 264.

In yet another example, the arrangement is asymmetrical with respect to the longitudinal axis L; in other words, the center of the valve 264 is positioned offset from the longitudinal axis L, i.e. the central hole of the connector module 243 is offset with respect to the longitudinal axis L. As a result, the fluid flow path is modified. For instance, due to the asymmetry, the fluid is provided with more space at one section of the valve 264, than at another section and therefore the fluid enters the dosing chamber in asymmetrical manner. This can be advantageous as it can reduce the creation of bubbles or air pockets in the fluid.

Figure 29:
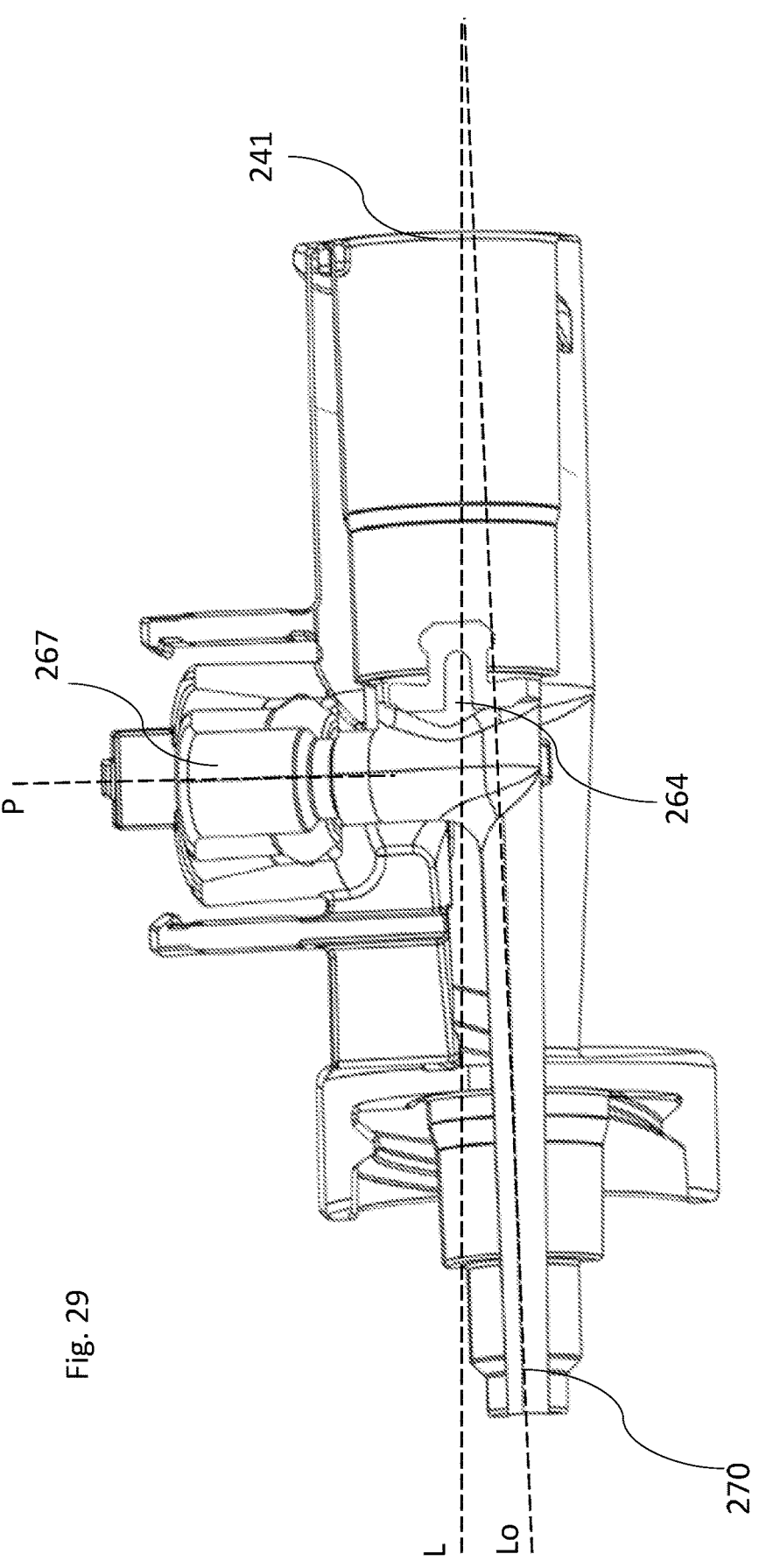
FIG. 29 shows a perspective view of the cross section of the embodiment of FIG. 22.

In another example shown in FIG. 29, the alignment of the central axis of the medicament container 29 is offset with respect to the dosing chamber inlet 240 and the dosing chamber outlet is offset with respect to the medicament delivery member 225. One advantage of this offset alignment is better visibility of potential air pockets and air bubbles within the dosing chamber 263. As will be described later, before the micro dosing device 20 is used, it has to be prepared by priming. During priming, the creation of air pockets of air bubbles within the therapeutic fluid is possible when the therapeutic liquid is used to flush through the micro dosing device in order to evacuate air out of the fluid path. The user verifies during priming if air pockets of bubbles are visible by looking through the transparent housing 283 and the transparent micro dosing unit 26. The offset alignment allows the user to spot the air bubbles and pockets more easily.

The fluid follows a fluid passage 265 through the dosing mechanism. The dosing chamber 263 comprises a fluid inlet on the distal side of the dosing chamber. The fluid inlet of the dosing chamber is the fluid outlet of the one-way valve 264. The connector unit 262 comprises a dosing chamber outlet 270, adjacent to the medicament delivery member 22. Optionally, a second one-way valve 222 as shown in FIG. 11 (or alternatively a sealing member), may be arranged after the dosing chamber outlet 270 in order to tightly seal the connection between the medicament delivery member 22 and the dosing unit 26.

Additionally or alternatively, a filter unit 220 may be placed before the medicament delivery member so as to retain possible crystalline or particle elements floating in the fluid.

Further, for the second one-way valve 222, a variety of valve types can be used. For example, in FIG. 26D a cone valve 222c is illustrated and in FIG. 26B an inverted cone valve 222b is depicted.

FIGS. 26A, 26C and 26E show alternative sealing members. For instance, in FIG. 26A the dosing chamber outlet 270 further comprises a circumferential recess configured to receive a circular seal, in this case an O-ring seal 222a.

FIG. 26C shows an alternative method for sealing the dosing chamber outlet 270. The dosing chamber outlet comprises at the proximal end a circumferential notch such that the notch is compressed when a force is applied evenly to the notch. As can be seen in FIG. 26C, when the end of the dosing chamber outlet with the notch is introduced into a medicament delivery member 224, the notch is compressed and the end of the dosing chamber outlet 270 seals the gap between the medicament delivery member 224 and the dosing chamber outlet 270.

Figures 30A, 30B, 30C, 30D, 30E, 30F:
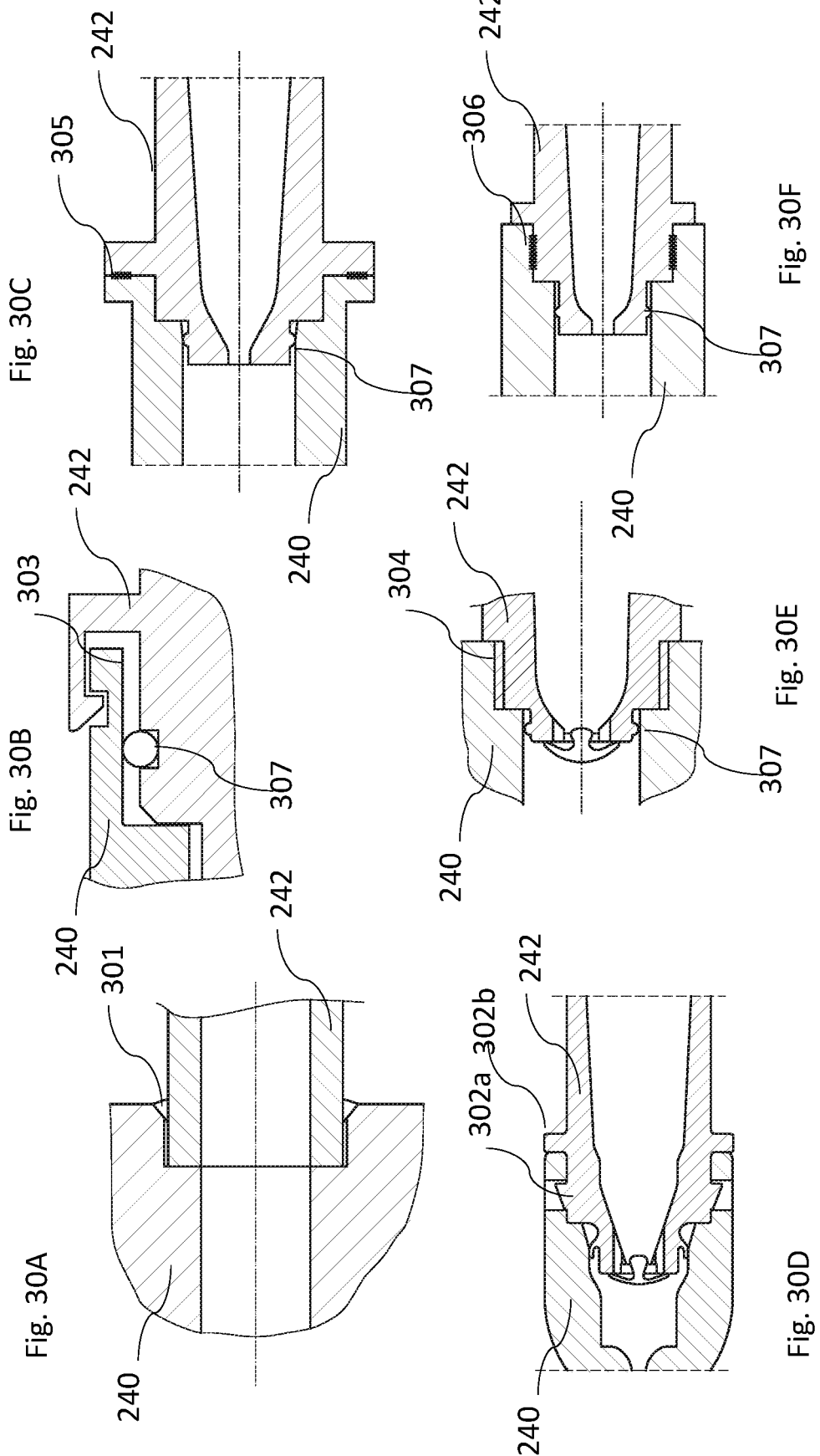
FIG. 30A to FIG. 30F show alternative connecting and locking means.

FIG. 30A to 30F further show alternative sealing elements and methods for securing and sealing the connector module 242 when the connector module is mounted on the connector unit 240. For instance, FIGS. 30A, 30C, 30D and 30F illustrate fixed irreversible mounting and sealing methods. In FIG. 30C an axial weld 305 connecting the connector with the connector module is shown, with a radial ring seal 307 circumferentially arranged around the connector module 242. In FIG. 30F a radial weld 306 of the connector with the connector module is shown, with a radial ring seal 307 circumferentially arranged around the connector module 242.

FIG. 30A shows an example of a glued or ultraviolet light cured bond 301 connecting the connector module 242 and the connector unit 240.

FIG. 30D illustrates a snap fit type connection. An angled protrusion 302a on the connector module 242 abuts a protrusion 302b of the connector unit 240, thus locking the connector module 242 to the connector unit 240.

FIG. 30B illustrates a bayonet connection 303 with a circumferential recess on the connector module 242 for receiving an O-ring seal 307.

FIG. 30E illustrates a threaded connection 304 connecting the connector module 242 to the connector unit 240.

The micro dosing mechanism (i.e. the activation unit) is in fluid communication with the dosing chamber 26 and extends radially or axially from the dosing chamber 263 on a perpendicular axis P that extends in a perpendicular direction with respect to the longitudinal axis L. The micro dosing mechanism further comprises a piston 268 positioned in a piston guide 272, whereby the piston rod 268 extends into the dosing chamber 263 and is connected to an activation mechanism 28. In one embodiment the piston 268 fits tightly into the guide 272 such that no fluid can penetrate between the guide walls and the piston 268.

In an alternative embodiment, the piston comprises a sealing member preventing the medicament fluid from penetrating the space between the guide and the piston rod 268. The piston is connected to an activation mechanism 28. In one example the activation mechanism is an activation button 28, and when a force applied on by a user for initiating the dose delivery, the force is directly transferred onto the piston 268. The activation mechanism further comprises a stop mechanism 282 arranged to bring the piston displacement to a halt even if the force is still acting on the piston 268.

Figure 17:
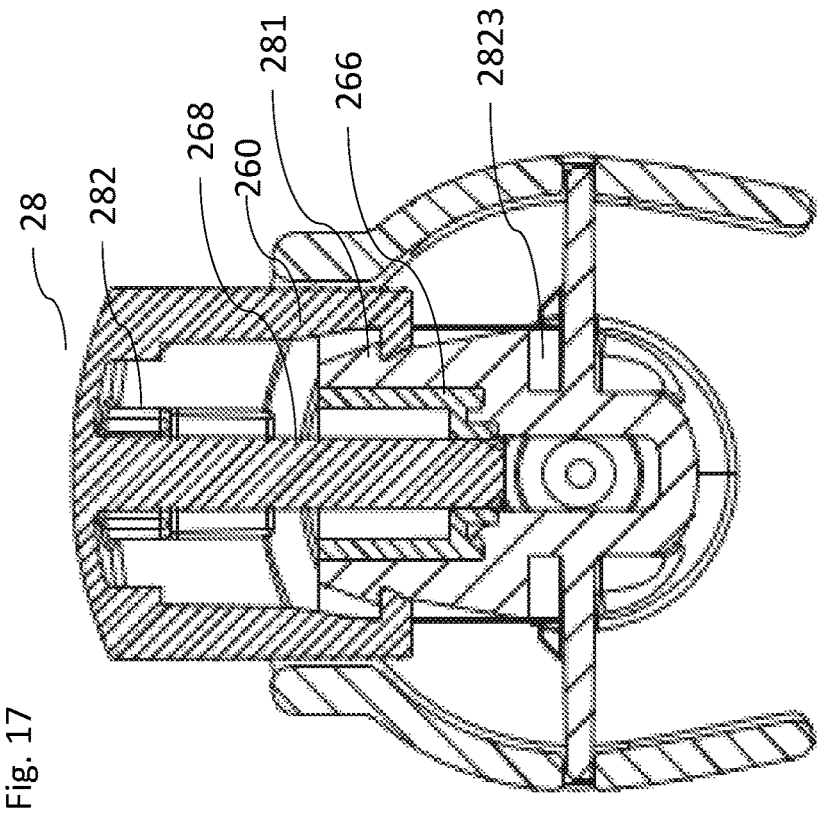
FIG. 17 is a cross sectional view of the device in FIG. 16.
Figure 16:
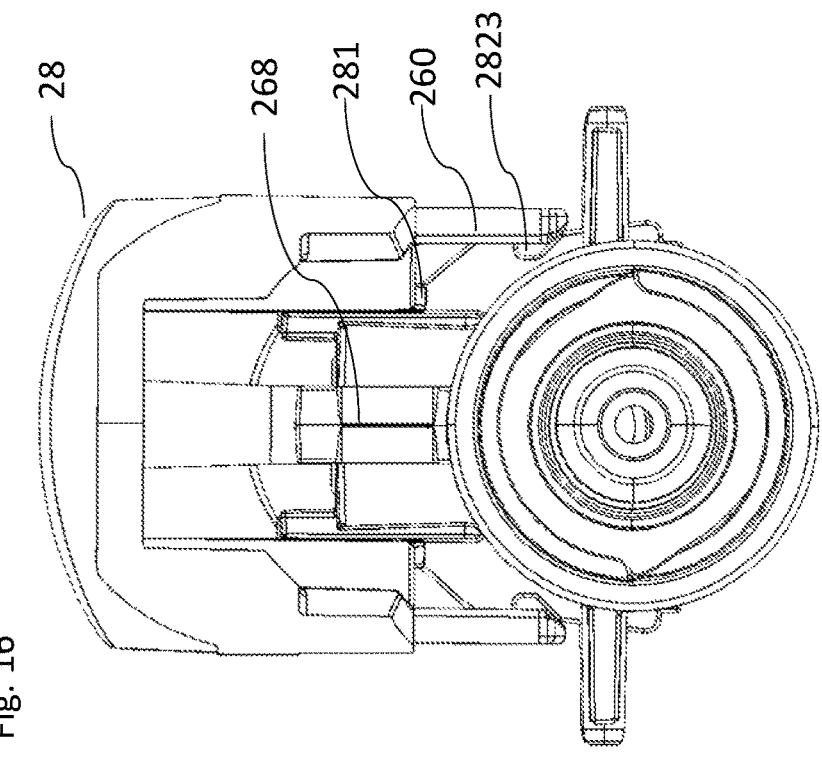
FIG. 16 shows the distal rear side of the micro dosing device of FIG. 14.
Figure 19:
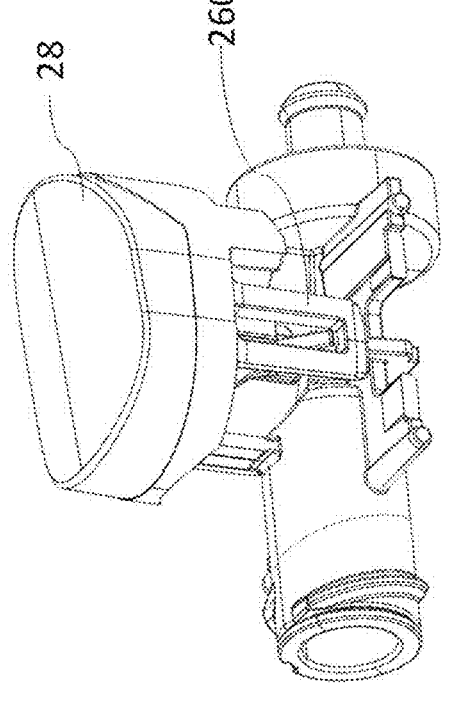
FIG. 19 shows a perspective view of the device of FIG. 14 without the housing.
Figure 21:
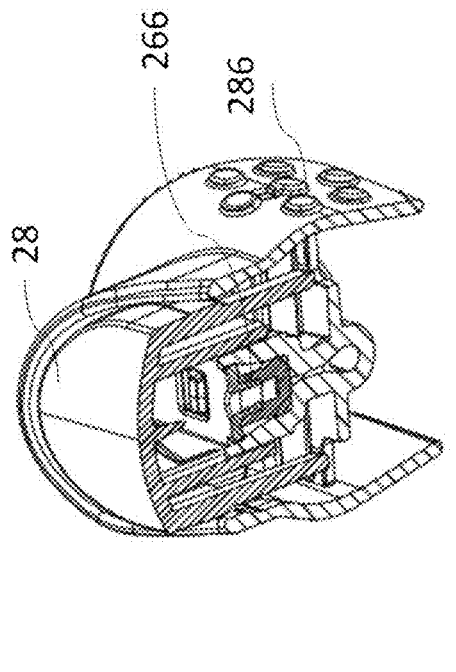
FIG. 21 shows a perspective view of the cross section of the device in FIG. 14.

In one example the activation button 28 comprises at least one longitudinal extension (arm 260) as shown in FIGS. 16, 17 and 19. In this example two arms are shown. The arms extend parallel to the piston rod, and the arms comprise gripping members or ledges 261. The arms 260 are engaged with protrusions 281 on the external side of the dosing chamber. The arms are thus locked and hold the activation button in place. Thus, the activation mechanism is securely held and prevented from accidental activation. When a force is applied onto the activation button 28, the button 28 moves towards the dosing chamber 263, displacing the piston rod 268 and thereby also displacing the longitudinal extensions 260. The arms 260 may flex outwardly and disengage from the protrusions 281, when the activation button is disengaged it can freely move forwards towards the dosing chamber 263.

In the example shown in FIG. 17, the ledges 261 of the arms are extended towards the axis P (i.e. inwardly) in order to engage with the protrusions 281 extending outwardly with respect to the axis P. Alternatively (and not shown in the figures), the mechanism can be rotated by 90 degrees, i.e. the ledges 261 and the protrusions 281 may extend in the direction of the longitudinal axis L. In this arrangement, the arms 260 flex in the direction parallel to the longitudinal axis L when the activation button is actuated.

As shown in the cross-sectional view in FIG. 17, the activation mechanism covers the perpendicular opening 267 of the dosing chamber 263, providing an activation button 280 on the outer surface of the activation mechanism 28. On the inner surface of the activation button 280 a recess for the piston rod is configured to receive and securely attach the piston rod 268 to the activation mechanism.

In one embodiment of the activation mechanism, the cover element comprising the activation button 280 and the piston rod 268 is an integral element, for example molded as one piece.

Figures 22, 23A, 23B, 23C:
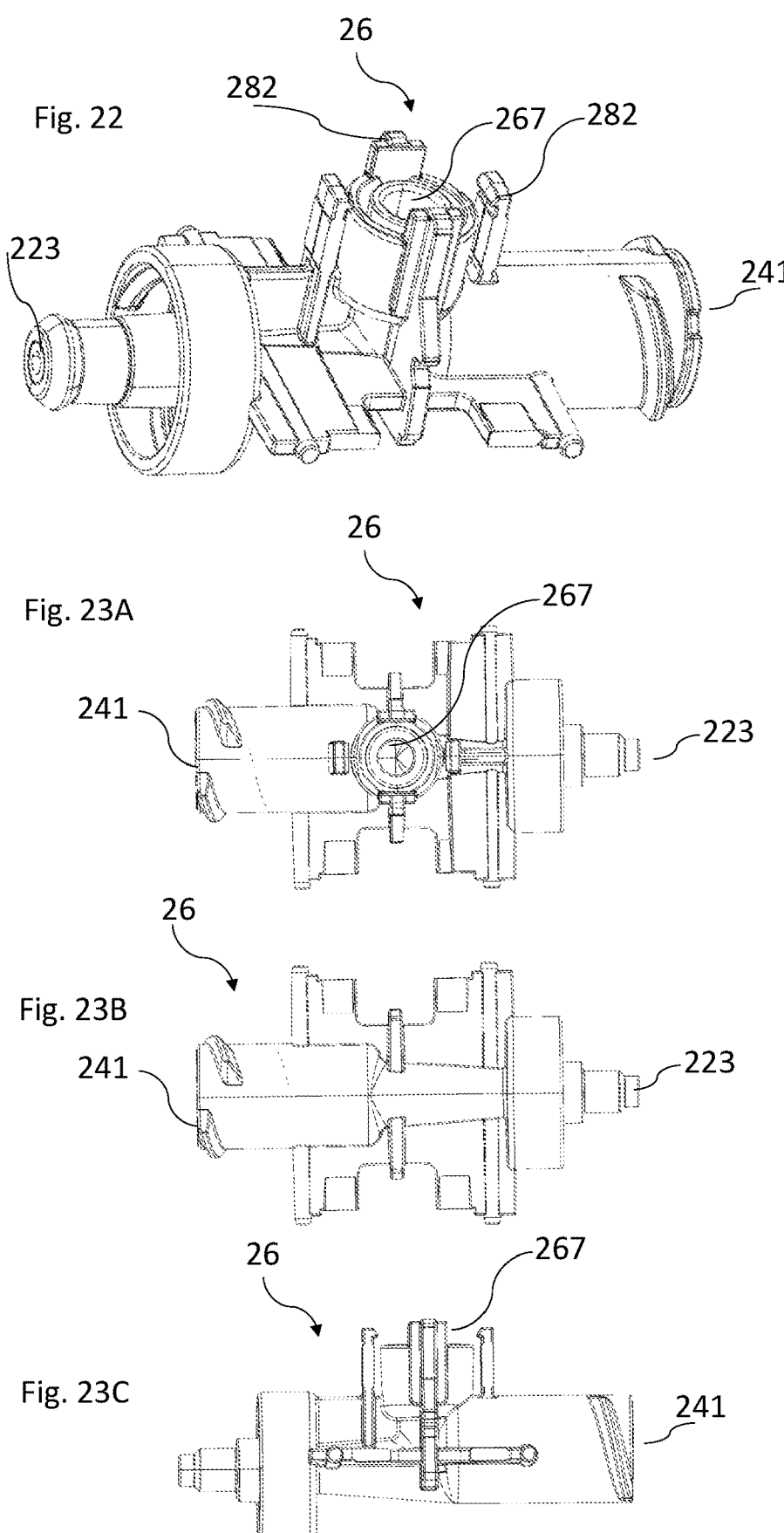
FIG. 22 shows a perspective view of the dosing chamber of the embodiment in FIG. 14.
FIG. 23A shows a view from above of the dosing chamber in FIG. 22.
FIG. 23B shows a view from below of the dosing chamber in FIG. 22.
FIG. 23C shows a side view of the dosing chamber in FIG. 22.
Figure 24:
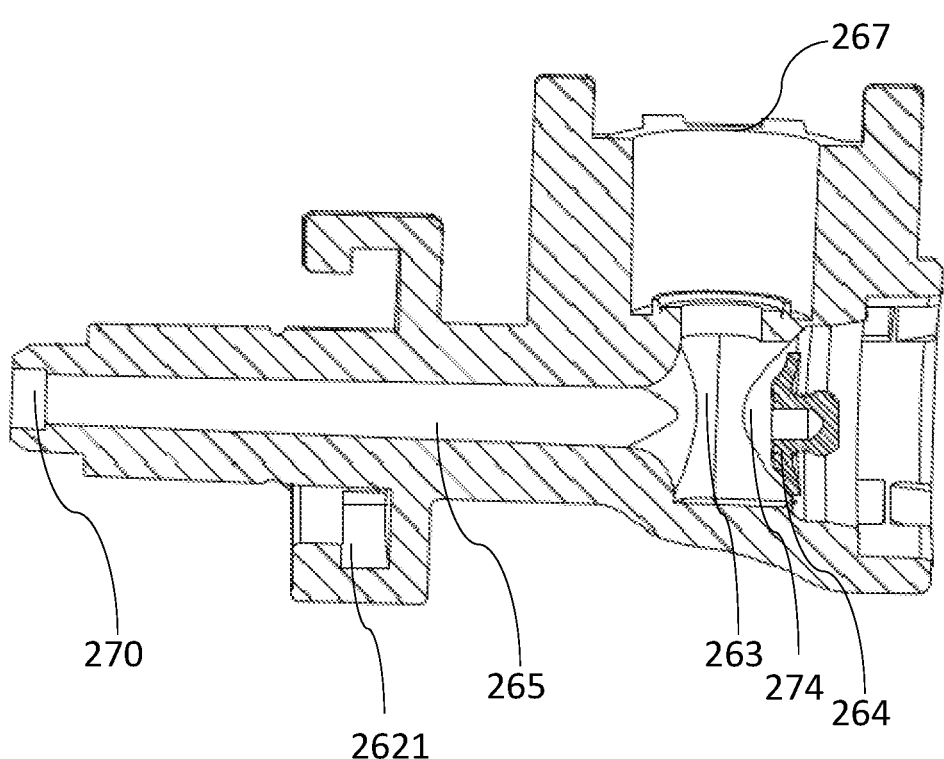
FIG. 24 shows a cross sectional view of the embodiment in FIG. 22.
Figure 25:
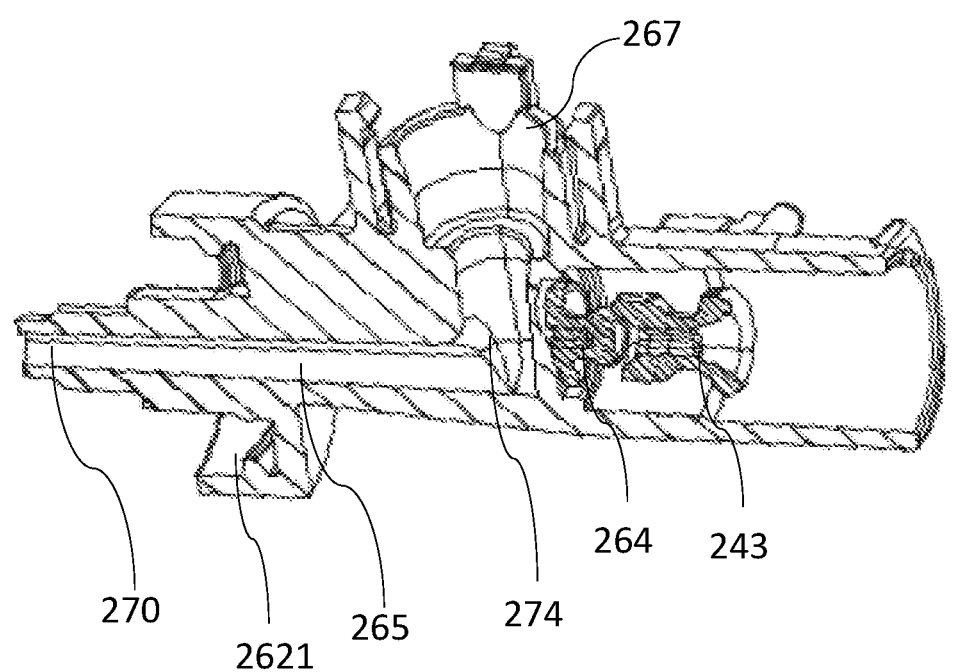
FIG. 25 shows a perspective view of the cross-sectional view of the embodiment in FIG. 22.
Figure 26:
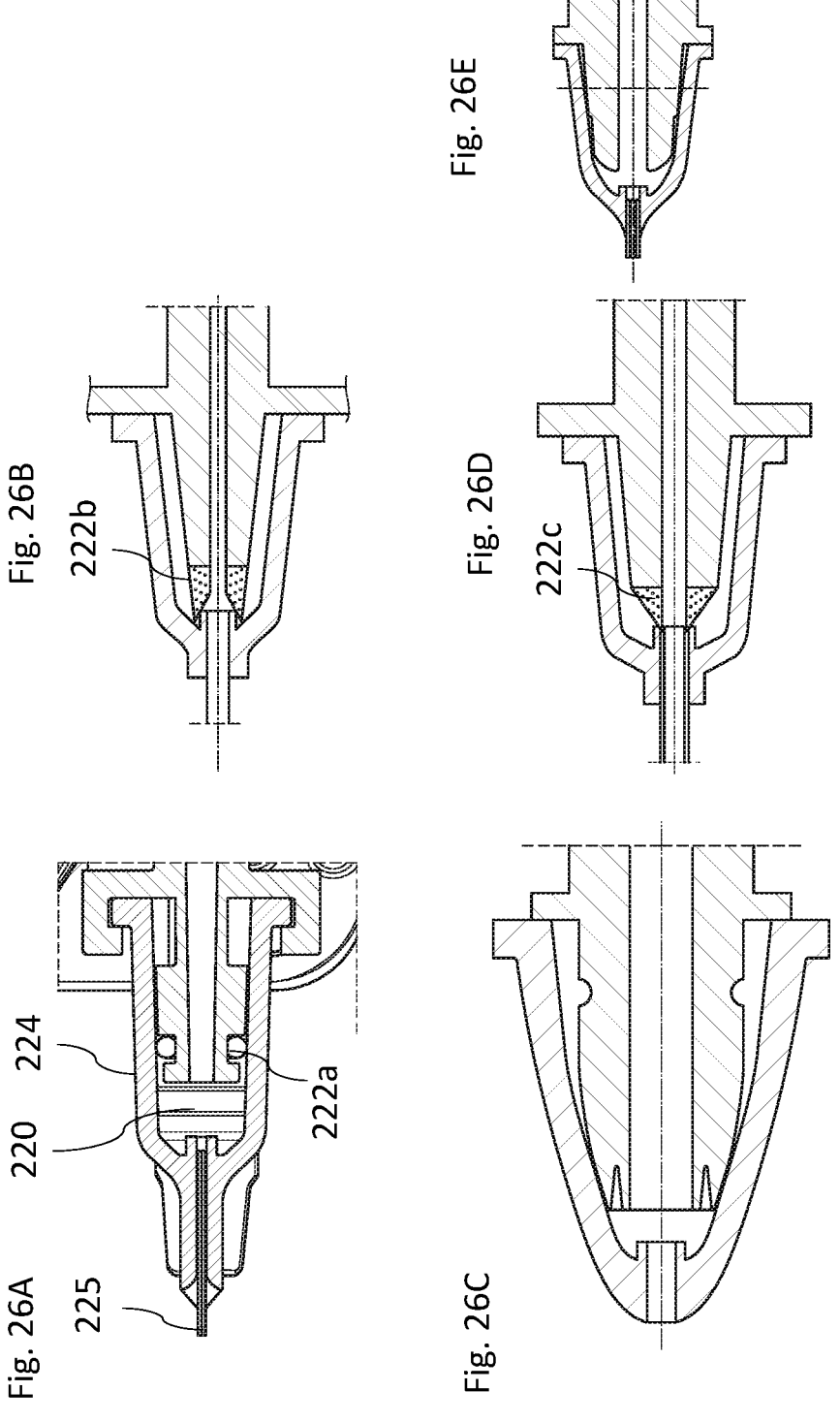
FIG. 26A to FIG. 26E show alternative proximal connecting means.

As shown in FIGS. 22 and 23 the dosing chamber unit 26 of this example is molded as one piece or, alternatively, the dosing chamber may be of a modular type assembled in an air and liquid tight manner. For example, it may be glued or welded together.

The initial state of the micro dosing device is shown in FIG. 17. the activation mechanism (i.e. the activation button 280) has not been pushed by a user and the lateral arms 260 with the ledges 261 are in an initial position, engaging the edge of the recesses 281 on the side wall of the dosing unit 26.

In the final state, when the exact amount of medicament dose volume has been expelled, the activation button 280 is stopped for example by abutting the edges of the opening 267 with stopping members 282 in the form of protrusions extending outwardly from the inwardly directed side of the activation button 280. Alternatively, as illustrated in FIG. 22, the stopping members are in the form of protrusions extending outwardly from the dosing chamber opening 267. The stopping mechanism may for example be a structural stopper, such as a layer or protrusion, wherein the layer or protrusion is arranged such as to halt the displacement of the piston rod a predefined position.

The stopping mechanism 282 may further comprise haptic and/or acoustic feedback. For example, when the circumferential element impacts the edge of the piston guide the user may hear a clicking sound and feel opposing force. Alternatively or additionally, the flexing of the arms into the final position, when engaging with a protrusion at the final stage, generates an acoustic signal.

One aspect of the micro dosing mechanism is that the piston displacement corresponds to a precise volume of the medicament to be delivered. In other words, the volume of the piston 268 extending and moving into the dosing chamber 263 under the applied force displaces the equivalent amount of medicament volume intended to be expelled.

When the exact amount of medicament volume dose has been expelled, the activation button 28 reaches the stopping mechanism 282. The stopping mechanism may for example be a structural stopper, like a layer or protrusion. In one example, the stopping mechanism are protrusions 2823 into which the lateral arms 260 can flex and can further securely be held in place such that the activation button mechanism is irreversibly locked in place. This is illustrated in FIG. 17 showing lateral arms 260 in an initial position before use and in FIG. 16 showing the lateral arms engaged with the protrusions 2823 in a final position. Optionally, a protective cover 288 may protect the activation mechanism from being accidentally activated. For example, the cover 288 encloses the activation mechanism and optionally may have protrusions capable of locking the activation button.

In further examples as shown in FIG. 33A, 33B, the protective cover 288 can be replaced by a protective cap 289 only enclosing the activation button 28. Also, a separate protective needle cap 290 as shown in FIG. 33A is an alternative solution for protecting the medical dosing device 20.

The activation mechanism 28 can further comprise a visual, acoustic or tactile signal for informing the user that the therapeutic fluid has been expelled. For example, when the arms 260 flex into the stopping mechanism a click sound may be generated, and a tactile sensation of a halt of the mechanism can be felt. The displacement of the activation button with respect to the protrusion 284 of housing 283, wherein the protrusion 284 forms a seating for the activation button, indicates visually that the activation mechanism has been actuated. For example, as shown in FIG. 9, the circumferential protrusion extends around the activation button, and has the same height at the proximal side as the activation button in the initial non activated state. From the proximal side, the protrusion decreases in height towards the distal side such that on the distal side the activation button is higher than the circumferential protrusion 284. When the activation button is pushed towards the dosing chamber, the activation button decreases its height with respect to the protrusion 284. This difference in height indicates visually that the activation button has been actuated. Additionally, the side of the circumferential protrusion 284, which faces the activation button and is not visible in the initial state, may further comprise a visual highlighting element, for example a signal colour a label, or both. This colour and/or label is only visible after the actuation of the activation button and the expelling mechanism.

Further examples of visual feedback indicators are shown in FIG. 34A to 34G. In FIG. 34A a rotating element 310 that rotates with respect to an indication mark 311 on the button shows the displacement on the button 28. FIG. 34B illustrates an indicator arranged perpendicular to the longitudinal axis.

FIG. 34C illustrates a security cap 312 with a breaking line point welded, wherein the security cap 312 is arranged below the activation button.

FIG. 34D another security cap 313, arranged on the activation button, wherein the security cap 313 comprising an integrity seal that breaks on rotation.

FIGS. 34E and 34F show integrated integrity seals 314, 315 on the button (FIG. 34F) or on the protective housing (FIG. 34E).

FIG. 34G shows the mechanism of an optional integrity pin 309 to indicate damage of the button when broken off and to prevent button movement during transport.

The micro dosing mechanism may further comprise a sealing member 266 which is introduced into the piston guide for compensating any tolerances of the rigid structural parts. The sealing member 226a as shown in FIG. 32A further comprises a tapering fringe 266a1 extending into the dose chamber, thereby providing a fluid-tight sealing of the dose chamber 263.

In one embodiment the dosing chamber 263 may optionally comprise side walls with a hydrophilic coating. In another embodiment, the dose unit is made of a material having hydrophilic properties.

In one embodiment the dosing chamber has a streamlined shape 274 such that the fluid as displaced is not compressed but instead smoothly guided to the delivery site. For example, the streamlined form of the side walls may prevent turbulence in the fluid flow; turbulence is known to enhance the creation of air pockets, bubbles or foam. Any kind of locked air either within the device or the liquid could alter the functionality and should be avoided in medical applications.

In one embodiment, the micro dosing device is configured for a single use and to provide a single dose, after which the activation mechanism is irreversibly locked.

In an alternative embodiment, the micro dosing device may be configured for multiple dose deliveries. In this example the activation mechanism may comprise a resilient member instead of the locking means 282, such that after a first dose delivery the activation mechanism may be reset to the initial position, allowing subsequent dose deliveries. In this example the medicament container is chosen to provide the required amount of subsequent dosages.

The method for assembly and use of the micro dose delivery device 20 comprises the step of mounting the medicament container 29 on the connector unit 240 by a turning movement of the user if a releasable threaded lock mechanism is used. Alternatively, the connector adapter 242 may be used to adapt the locking mechanism of the medicament container 29 to the locking mechanism 276 of the dosing unit 26, and then mounted onto the dosing unit 26. Then the medicament delivery member 22 is mounted on the connector 262 at the proximal side 2b of the dosing unit 26. The sequence or order of the above steps may optionally be reversed. When the medicament delivery member 22 and the medicament container 29 are securely mounted on the connectors 262, 240 of the dosing unit 26, a fluid connection between the medicament container 29 and the medicament delivery member 22 via the dosing chamber 263 of the dosing unit 26 is established.

Subsequently the medicament container 29 is actuated by the user to dispense the medicament into the dosing chamber 263 until the medicament is released at the medicament delivery member 22. As a result, all fluid flushes through the available spaces until all volumes are filled with the medicament fluid. In other words, the dosing chamber 263, the fluid guides 265 the dosing chamber outlet 270 and the medicament delivery member outlet (for example the needle 225), are all filled with the fluid. Accordingly, any subsequent fluid displacement does not depend on the needle volume or the fluid guide and outlet volume.

It is to be understood that the assembly of the micro dosing device 20 should typically be performed in antiseptic or sterile conditions.

One advantage of the micro dosing device 10, 20 is that different needle sizes with different needle volumes may be used without adapting the dosing mechanism to the needle volume. Another advantage is that potential air pockets or bubbles can more easily be expelled at the medicament delivery member outlet.

Once the micro dosing device 20 is assembled as outlined above, the medicament can be expelled as an exact dose volume when the user actuates the micro dosing mechanism by pushing on the activation button 28.

While various aspects and embodiments have been disclosed herein, other aspects and embodiments will be apparent to those skilled in the art. All embodiments within and between different aspects of the devices and methods can be combined unless the context clearly dictates otherwise. The various aspects and embodiments disclosed herein are for purposes of illustration and are not intended to be limiting, with the true scope and spirit being indicated by the claims.

The invention claimed is:

1. A micro dosing device for delivering a metered dose of a therapeutic fluid, the micro dosing device comprising:
a dosing unit comprising a dosing chamber;
a distal connector unit at a distal end for fluidly connecting a medicament container to the dosing chamber;
a proximal connector unit at a proximal end for fluidly connecting the dosing chamber to a medicament delivery member; and
an activation mechanism,
wherein the dosing chamber is configured to receive a therapeutic fluid,
wherein the micro dosing device comprises a first dosing mechanism, the dosing mechanism providing an exactly metered dose of fluid to be expelled by the medicament delivery member when triggered by the activation mechanism,
wherein the activation mechanism comprises a piston rod liquid tightly slidably fitted in a piston guide wherein the piston rod has a predefined rod volume, so that when actuated, the piston rod moves into the dosing chamber, wherein the displacement volume of the piston rod defines the metered dose volume to be expelled upon actuation and displacement of the piston rod into the dosing chamber, and
wherein the activation mechanism comprises one or more lateral arms extending respectively along a lateral side of the activation button, wherein the lateral arms each comprise a ledge at their terminal portion, the ledge being configured to engage with a respective recess of a corresponding lateral side of the dosing unit.

2. The micro dosing device of claim 1, wherein the activation mechanism comprises an activation member and a second dosing mechanism, wherein the activation mechanism extends radially from the dosing chamber, and wherein the activation member is coupled to the piston rod and displaces the piston rod upon actuation of the activation member by a user.

3. The micro dosing device of claim 2, wherein the dosing mechanism is a circumferential stopping member comprising a predefined perpendicular extension with respect to the longitudinal axis L, wherein the radial extension is defined by the radial extension of the piston guide such that the circumferential stopping member abuts the piston guide when displaced by the activation button, and wherein the predefined perpendicular extension is defined such that the displacement of the piston rod comes to a halt at a predefined displacement volume.

4. The micro dosing device of claim 3, wherein the circumferential stopping member is a modular element predefining the dosing volume to be expelled by the dosing unit.

5. The micro dosing device of claim 3, wherein an audible click is provided by the stopping member when coming to a halt and abutting the edge of the piston guide, indicating a user the end of dose.

6. The micro dosing device of claim 3, wherein the circumferential stopping member is an integral part of the activation mechanism, and wherein the activation member and the stopping member are integral.

7. The micro dosing device of claim 1, wherein the first one-way valve arranged at the dosing chamber inlet and the micro dosing device further comprises a second one-way valve, wherein the first and the second one-way valve are configured to regulate the fluid flow in one direction, minimizing backflow.

8. The micro dosing device of claim 7 wherein the distal connector unit further comprises an adapter module connected to a connector, wherein one-way valve at the dosing chamber inlet is arranged offset with respect to the longitudinal axis L.

9. The micro dosing device of claim 8, wherein in a final state, each of the ledges engage with a second respective recess, locking the activation button in a final state.

10. The micro dosing device of claim 1, wherein the dosing chamber further comprises streamlined inner surfaces which are optimized to reduce inner dead volumes, wherein the surface geometry has a form for improving fluid flow characteristics.

11. The micro dosing device of claim 1, wherein the distal connector unit is arranged offset with respect to the longitudinal axis L, such that the proximal connector unit is not coaxial with the distal connector unit.

12. The micro dosing device of claim 11, wherein each ledge is in contact with the respective recess at an initial non activated state, and after activation and expelling of the predefined dose volume of fluid, the ledge is displaced further apart from the recess, such that a visual feedback indicates that the therapeutic fluid has been expelled.

13. The micro dosing device of claim 1, wherein the activation mechanism further comprises a resilient member acting on the activation mechanism to reset the displacement of the dosing mechanism and the piston rod.

14. The micro dosing device of claim 1, wherein the distal connector unit at the distal end is an integral part of the dosing unit.

15. The micro dosing device of claim 1, wherein the proximal connector unit at the proximal end comprises a portion which is an integral part of the dosing unit, wherein the dosing unit is an integral part, and wherein the dosing unit comprises a modular part which can receive and hold a variety of connecting modules with different connector means.

16. The micro dosing device of claim 1, further comprising an adapter module for the distal connector unit, the adapter module being configured to be held within the distal opening of the connector unit and to provide connecting means for the medicament container such that different diameters or locking mechanisms of the medicament container can be adapted to the micro dosing device.

17. A method for use and assembly of a micro dosing device according to claim 1 comprising the steps of:

mounting the medicament delivery member in the medicament delivery connector at a proximal end of the dosing unit;

mounting a medicament container into a medicament container connector at the distal end of the dosing unit;

activating an expelling mechanism of the medicament container;

expelling the medicament fluid into the dosing unit;

activating the activation mechanism by applying a force onto the activation member for expelling the metered volume of medicament at the medicament delivery member wherein none of the steps are reversible.

18. A system comprising a micro dosing device according to claim 1 and a container comprising a liquid pharmaceutical preparation, wherein the container is connected to the medicament container connector.

19. The system according to claim 18, wherein the micro dosing device is preassembled on the container.

* * * * *